(12) United States Patent
Sucheck et al.

(10) Patent No.: US 9,527,952 B1
(45) Date of Patent: Dec. 27, 2016

(54) AMORPHOUS POLYESTER FROM BIO-BASED BIS-FURAN ASSEMBLY

(71) Applicant: The University of Toledo, Toledo, OH (US)

(72) Inventors: Steven Sucheck, Maumee, OH (US); Vishwanath Gaitonde, Toledo, OH (US); Maria Coleman, Toledo, OH (US)

(73) Assignee: The University of Toledo, Toledo, OH (US)

( * ) Notice: Subject to any disclaimer, the term of this patent is extended or adjusted under 35 U.S.C. 154(b) by 0 days.

(21) Appl. No.: 14/621,520

(22) Filed: Feb. 13, 2015

Related U.S. Application Data

(60) Provisional application No. 61/940,637, filed on Feb. 17, 2014, provisional application No. 61/940,545, filed on Feb. 17, 2014.

(51) Int. Cl.
| | | |
|---|---|---|
| C08G 63/16 | (2006.01) | |
| C08G 64/30 | (2006.01) | |
| C08G 63/00 | (2006.01) | |
| C07D 307/44 | (2006.01) | |
| C07D 307/50 | (2006.01) | |
| C08G 63/78 | (2006.01) | |

(52) U.S. Cl.
CPC ............ *C08G 63/16* (2013.01); *C07D 307/44* (2013.01); *C07D 307/50* (2013.01); *C08G 63/00* (2013.01); *C08G 63/78* (2013.01); *C08G 64/305* (2013.01)

(58) Field of Classification Search
CPC ... C07D 307/42; C07D 307/46; C07D 307/50; C07D 307/44; C08K 5/1535; C08G 63/16; C08G 63/00; C08G 63/78; C08G 64/305
See application file for complete search history.

(56) References Cited

U.S. PATENT DOCUMENTS

| | | | |
|---|---|---|---|
| 2,681,917 | A | 6/1954 | Fauque |
| 3,435,003 | A | 3/1969 | Craven |
| 3,509,103 | A | 4/1970 | Teague |
| 4,391,946 | A | 7/1983 | Akerberg et al. |
| 4,426,460 | A | 1/1984 | Pentz |
| 5,260,378 | A | 11/1993 | Gandini et al. |

OTHER PUBLICATIONS

Abid et al., "Polyamides incorporating furan moieties. 5. Synthesis and characterisation of furan-aromatic homologues", Polymer, 2004, vol. 45, pp. 5793-5801.
Belgacem et al., "Urethanes and Polyurethanes Bearing Furan Moieties-3. Synthesis, Characterization and Comparative Kinetics of the Formation of Diurethanes", European Polymer Journal, 1993, vol. 29, No. 9, pp. 1217-1224.
le;3qBoufi et al., "Urethanes and Polyurethanes Bearing Furan Moieties-4. Synthesis, Kinetics, and Characterization of Linear Polymers", Macromolecules, 1993, vol. 26, pp. 6706-6717.
Boufi et al., "Urethanes and Polyurethanes Bearing Furan Moieties-5. Thermoplastic elastomers based on sequenced structures", Polymer, 1995, vol. 36, No. 8, pp. 1689-1696.
Gandini, "Furans as offspring of sugars and polysaccharides and progenitors of a family of remarkable polymers: a review of recent progress", Polymer Chemistry, 2010, vol. 1, pp. 245-251.
Gandini et al., "Furans in Polymer Chemistry", Progress in Polymer Science, 1997, vol. 22, pp. 1203-1379.
Gandini, "The furan/maleimide Diels-Alder reaction: A versatile click-unclick tool in macromolecular synthesis", Progress in Polymer Science, 2013, vol. 38, pp. 1-29.
Gandini et al., "Materials from renewable resources based on furan monomers and furan chemistry: work in progress", Journal of Materials Chemistry, 2009, vol. 19, pp. 8656-8664.
Gandini, "Polymers from Renewable Resources: A Challenge for the Future of Macromolecular Materials", Macromolecules, 2008, vol. 41, No. 24, pp. 9491-9504.
Gharbi et al., "Polyamides incorporating furan moieties. 1. Interfacial polycondensation of 2,2-bis(5-chloroformyl-2-furyl)propane with 1,6-diaminohexane", Acta Polymerica, 1999, vol. 50, pp. 293-297.
Gomes et al., "Synthesis and Characterization of Poly(2,5-furan dicarboxylate)s Based on a Variety of Diols", Journal of Polymer Science Part A: Polymer Chemistry, 2011, vol. 49, pp. 3759-3768.
Khrouf et al., "Polyesters bearing furan moieties", Polymer Bulletin, 1996, vol. 37, pp. 589-596.
Laita et al., "The application of the Diels-Alder Reaction to polymers bearing Furan Moieties. 1. Reactions with Maleimides", European Polymer Journal, 1997, vol. 33, No. 8, pp. 1203-1211.
Maktouf et al., "Polyamides based on furanic diamines and aromatic dianhydrides: synthesis, characterization and properties", Polymer Bulletin, 2011, vol. 67, pp. 1111-1122.
Mitiakoudis et al., "Synthesis and Characterization of Furanic Polyamides", Macromolecules, 1991, vol. 24, pp. 830-835.
Moore et al., "Polyesters Derived from Furan and Tetrahydrofuran Nuclei", Macromolecules, 1978, vol. 11, No. 3, pp. 568-573.
Moore et al., "Polymerization of furandicarbonyl chloride with bisphenol A poly(2,5-furandiylcarbonyloxy-1,4-phenylenedimethylmethylene-1,4-phenyleneoxycarbonyl)", Polymer, 1979, vol. 20, pp. 627-628.
Moore et al., "Poly[2,5-furan diylcarbonyloxymethylene(2,5-dihydro-2,6-furan diyl)methyleneoxycarbonyl]", Journal of Polymer Science: Polymer Chemistry Edition, 1978, vol. 16, pp. 2407-2409.

(Continued)

*Primary Examiner* — Ling Choi
*Assistant Examiner* — Gennadiy Mesh
(74) *Attorney, Agent, or Firm* — MacMillan, Sobanski & Todd, LLC

(57) ABSTRACT

Polymers, including Polyesters and Polycarbonates comprising residue of bis-furan diol, which is produced from renewable furfural feedstock and methods of making and using of those polyesters and polycarbonates are described. The method includes reacting a bis-furan diol with a dicarboxylic acid in the presence of a carbodiimide to produce the bis-furan containing polymers. In certain embodiments, the dicarboxylic acid is succinic acid; the bis-furan diol is the 5,5'-(propane-2,2-diyl)bis(furan-2,5-diyl) dimethanol and the carbodiimide is of N,N-diisopropylcarbodiimide.

5 Claims, 30 Drawing Sheets

(56) References Cited

OTHER PUBLICATIONS

Moore et al., "Polyhydroxymethlyfuroate[Poly(2,5-furandiylcarbonyloxymethylene)]", Journal of Polymer Science: Polymer Chemistry Edition, 1984, vol. 22, pp. 863-864.

Moreau et al., "Recent catalytic advances in the chemistry of substituted furans from carbohydrates and in the ensuring polymers", Topics in Catalysis, 2004, vol. 27, Nos. 1-4, pp. 11-30.

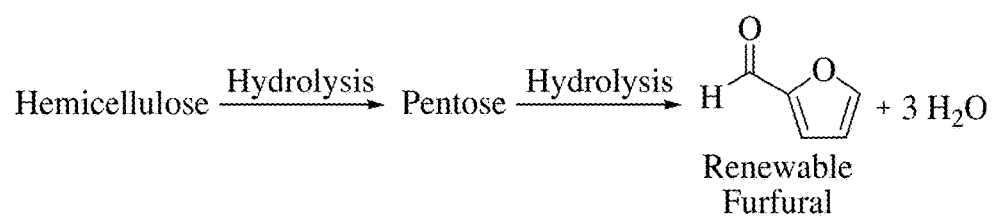
FIG. 1A
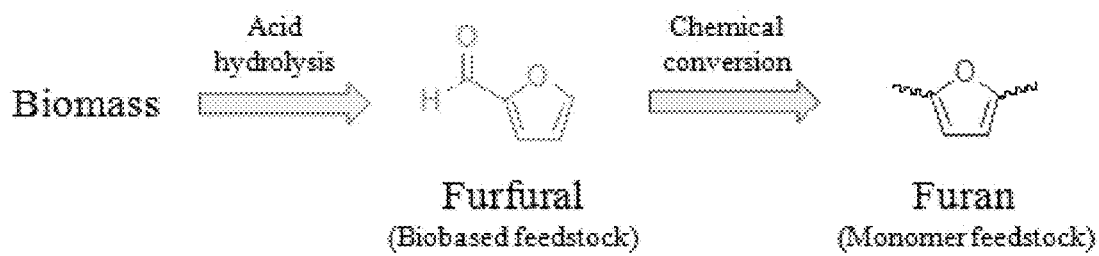
PRIOR ART FIG. 1B

R = Methyl, Ethyl, Phenyl

A

B

C

D

E

F

G

AMORPHOUS POLYESTER FROM BIO-BASED BIS-FURAN ASSEMBLY

RELATED APPLICATIONS

This application claims priority to U.S. Provisional Application Ser. No. 61/940,637, filed under 35 U.S.C. §111(b) on Feb. 17, 2014, and U.S. Provisional Application Ser. No. 61/940,545, filed under 35 U.S.C. §111(b) on Feb. 17, 2014, the disclosures of which are incorporated herein by reference in their entirety.

STATEMENT REGARDING FEDERALLY SPONSORED RESEARCH

This invention was made with no government support. The government has no rights in the invention.

BACKGROUND OF THE INVENTION

Depleting fossil fuel reserves are currently escalating the exploration of renewable sources of material. The development of new renewable monomer feedstocks for the fabrication of next-generation polymeric materials is thus important to the future success of the polymer industry.

Lignocellulosic biomass plays a central role in renewable resources that contribute to a self-sustaining model for future polymer material demand. A significant percentage of biomass consists of non-food sources such as grass, wood, or straw, which can be utilized for producing value-added chemicals and polymers. The core constituents of lignocelluloses are principally cellulose, hemicellulose, and lignin. Hemicellulose is an amorphous, branched structure, which displays modest strength and undergoes acid hydrolysis to yield xylose. On further hydrolysis, xylose generates furfural with loss of three molecules of water, as shown in the reaction in FIG. 1A. The conversion of biomass to furfural, depicted in PRIOR ART FIG. 1B, is a known process used to access furan-based monomers and subsequently generate various bio-based polymers. However, there remains a need for additional types of polymeric materials made from furan-based monomers.

SUMMARY OF THE INVENTION

Provided herein is a composition comprising Formula I:

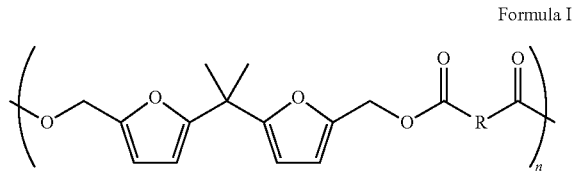

Formula I wherein R is $C_6H_4$ or $(CH_2)_x$ when x is from 1 to 10, and n is from 10 to 10,000; and salts, stereoisomers, racemates, polymorphs, solvates, and hydrates thereof.

In certain embodiments, the composition comprises monomeric units having a structural formula of Formula II:

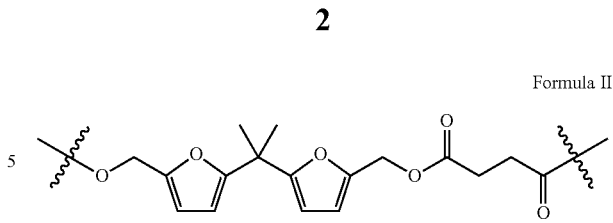

Formula II

In certain embodiments, the composition comprises Formula III:

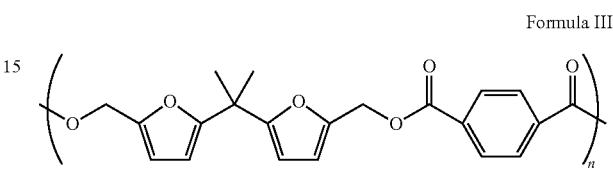

Formula III wherein n is from 10 to 10,000.

In certain embodiments, the composition comprises Formula IV:

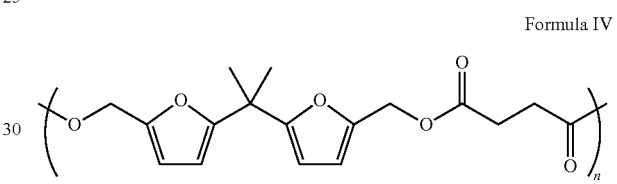

Formula IV wherein n is from 10 to 10,000.

In certain embodiments, the composition comprises monomeric units having a structural formula of Formula V:

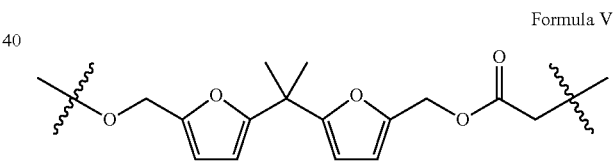

Formula V

In certain embodiments, the composition has a weight loss of about 2% at a temperature of about 100° C. In certain embodiments, the composition has a weight loss of about 5% at a temperature of about 225° C. In certain embodiments, the composition has a weight loss of about 20% at a temperature of about 266° C. In certain embodiments, the composition has a weight loss of about 48% at a temperature of about 329° C. In certain embodiments, the composition has a glass transition temperature in a range of from about 15° C. to about 25° C. In certain embodiments, the composition has a glass transition temperature of about 20° C. In certain embodiments, the composition is amorphous. In certain embodiments, liquefaction of the composition increases between about 110° C. and about 150° C. In certain embodiments, the composition is transparent at a temperature of about 190° C. In certain embodiments, the composition degrades at a temperature of about 270° C.

In certain embodiments, the composition has a mass distribution in a range of from about 0.5 kDa to about 7.5 kDa. In certain embodiments, the composition has repeating structures of 318 mass units. In certain embodiments, the composition has a polydispersity index of from about 1.00283 to about 1.04441. In certain embodiments, the composition has a number average molecular weight of from about 1709.29 g/mol to about 5205.14 g/mol. In certain embodiments, the composition has a weight average molecular weight of from about 1869.79 g/mol to about 5219.87 g/mol. In certain embodiments, the composition has a degree of polymerization of from about 5.3651 to about 16.3592. In certain embodiments, the average molecular weight of the composition is from about 3 kDa to about 5 kDa. In certain embodiments, the composition is characterized by an infrared spectrum having a peak at 1750 cm$^{-1}$. In certain embodiments, the composition is characterized a $^1$H NMR spectrum having peaks at δ 6.29, δ 5.97, δ 5.01, δ 2.64, and δ 1.63. In certain embodiments, the composition is characterized by a $^{13}$C NMR spectrum having peaks at δ 172.12, δ 160.73, δ 148.06, δ 111.61, δ105.64, δ 58.81, δ 37.78, δ 29.14, and δ 26.39.

Further provided herein is a composition comprising Formula VI:

Formula VI

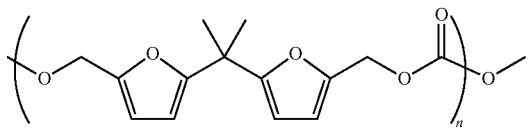

wherein n is from 10 to 10,000; and salts, stereoisomers, polymorphs, racemates, solvates, and hydrates thereof.

Further provided herein is a method of making a bis-furan polymeric material comprising the steps of: synthesizing a bis-furan derivative from furfural, wherein the bis-furan derivative is a bis-furan diol or a bis-furan diamide; and synthesizing a bis-furan polymeric material from the bis-furan derivative. In certain embodiments, the furfural is produced by subjecting lignocellulosic biomass to an acid hydrolysis to produce a furfural feedstock. In certain embodiments, the bis-furan polymeric material is selected from the group consisting of: polyesters, polyurethanes, polyurea, and polyamides. In certain embodiments, the bis-furan polymeric material consists essentially of a polyester.

In certain embodiments, the bis-furan derivative is a bis-furan diol synthesized by a method comprising the steps of: protecting aldehyde functionality in the furfural to obtain a protected furfural; heating the protected furfural in the presence of an acid to obtain a protected bis-furan compound; deprotecting the protected bis-furan compound to obtain a bis-furan dialdehyde; and reducing the bis-furan dialdehyde to obtain a bis-furan diol. In certain embodiments, the aldehyde functionality is protected by reacting the furfural with 1,2-ethanedithiol. In certain embodiments, the acid comprises H$_2$SO$_4$. In certain embodiments, the deprotecting comprises reacting the protected bis-furan compound with SeO$_2$. In certain embodiments, the reducing comprises reacting the bis-furan dialedhyde with NaBH$_4$. In certain embodiments, the bis-furan polymeric material is synthesized by reacting a bis-furan diol with an aliphatic or aromatic dicarboxylic acid in the presence of a carbodiimide. In certain embodiments, the dicarboxylic acid comprises succinic acid.

In certain embodiments, the bis-furan polymeric material is synthesized by an alcohol transesterification comprising reacting a bis-furan diol with a diester-containing compound in the presence of a catalyst. In particular embodiments, the diester-containing compound comprises dimethyl terephthalate.

In certain embodiments, the bis-furan polymeric material is synthesized by reacting a bis-furan diol with triphosgene in the presence of a base catalyst. In certain embodiments, the bis-furan polymeric material is synthesized by reacting a bis-furan diol with an aliphatic or aromatic carbonate ester in the presence of a base catalyst. In particular embodiments, the carbonate ester is selected from the group consisting of: dimethyl carbonate, diethyl carbonate, and diphenyl carbonate.

In certain embodiments, the method further comprises the step of producing a fabricated article from the bis-furan polymeric material.

Further provided is a bis-furan polymeric material produced from the method described herein.

Further provided is a method of producing a polymeric material comprising reacting a bis-furan diol with a dicarboxylic acid in the presence of a carbodiimide to produce a polymeric material. In certain embodiments, the dicarboxylic acid consists essentially of succinic acid. In certain embodiments, the bis-furan diol consists essentially of 5,5'-(propane-2,2-diyl)bis(furan-2,5-diyl)dimethanol. In certain embodiments, the carbodiimide consists essentially of N,N-diisopropylcarbodiimide.

BRIEF DESCRIPTION OF THE DRAWINGS

FIG. 1A: Scheme showing the conversion of hemicelluloses to furfural via pentose sugars.

PRIOR ART FIG. 1B: Scheme showing the production of furan-based monomer feedstock from biomass, via furfural.

FIG. 7B shows the scheme with these reagents and conditions labeled.

FIG. 13A shows weight loss (%) versus temperature (° C.), and FIG. 13B shows derivative weight (%/° C.) versus temperature (° C.).

DETAILED DESCRIPTION OF THE INVENTION

Figure 2:
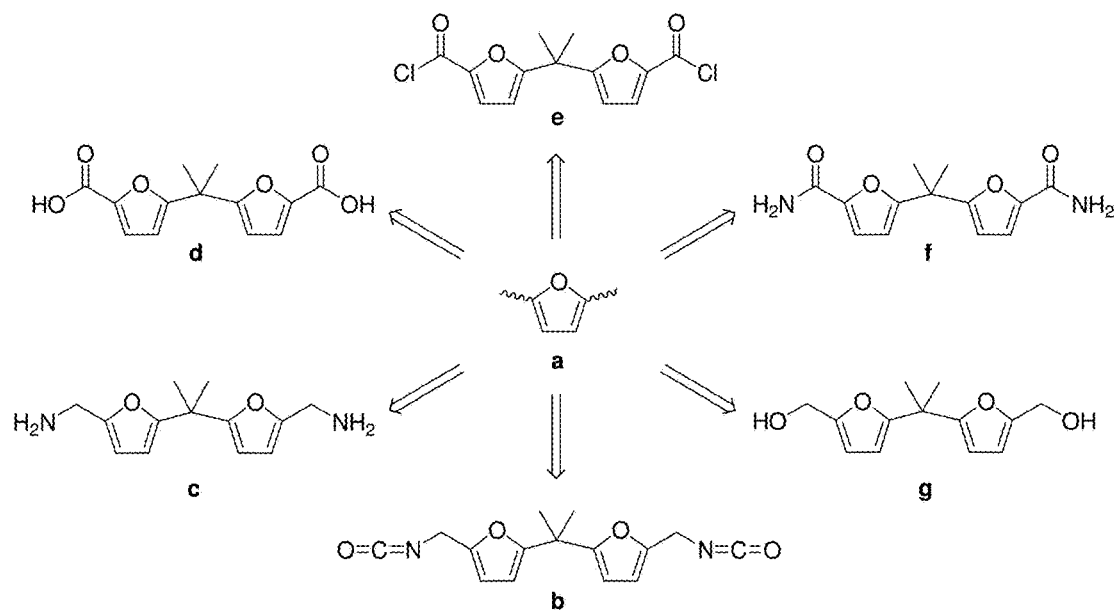
FIG. 2: Accessible BF-based derivatives: (a) parent furan, (b) BF-diisocyanate, (c) BF-diamine, (d) BF-diacid, (e) BF-diacid chloride, (f) BF-diamide, and (g) BF-diol.

Throughout this disclosure, various publications, patents and published patent specifications are referenced by an identifying citation. The disclosures of these publications, patents and published patent specifications are hereby incorporated by reference into the present disclosure in their entirety to more fully describe the state of the art to which this invention pertains.

Definitions

The term "self-healing" as used herein refers to the ability of a polymer to repair damage caused by mechanical stress or usage without external stimuli like heat, solvents, or plasticizers.

The term "solvate" refers to a solid form of a specified compound containing solvent molecules as part of the crystal structure. Solvates can have different solubilities, hygroscopicities, stabilities, and other properties. Examples of solvates include, but are not limited to, compounds in combination with water, isopropanol, ethanol, methanol, DMSO, ethyl acetate, acetic acid, or ethanolamine. Solvates are sometimes termed "pseudopolymorphs."

The term "hydrate" refers to a solvate with water.

The term "racemate" refers to a mixture that contains an equal amount of enantiomers.

It will be appreciated by one of ordinary skill in the art that asymmetric centers may exist in any of the compounds disclosed herein. Thus, the compounds presently described may be in the form of an individual enantiomer, diastereomer, or geometric isomer, or may be in the form of a mixture of stereoisomers. In certain embodiments, the compounds are enantiopure compounds. In certain other embodiments, mixtures of stereoisomers or diastereomers are provided. Additionally, the compounds encompass both (Z) and (E) double bond isomers (or cis and trans isomers) unless otherwise specifically designated. Thus, compounds generally depicted in structures herein encompass those structures in which double bonds are (Z) or (E).

It will be appreciated that any of the compounds described herein may be substituted with any number of substituents or functional moieties. In general, the term "substituted" whether preceded by the term "optionally" or not, and substituents contained in formulas, refer to the replacement of hydrogen atoms in a given structure with a specified substituent. When more than one position in any given structure may be substituted with more than one substituent selected from a specified group, the substituent may be either the same or different at every position.

As used herein, the term "substituted" is contemplated to include all permissible substituents of organic compounds. In a broad aspect, the permissible substituents include acyclic and cyclic, branched and unbranched, carbocyclic and heterocyclic, aromatic and nonaromatic substituents or organic compounds. For purposes of explanation herein, heteroatoms such as nitrogen may have hydrogen substituents and/or any permissible substituents of organic compounds described herein which satisfy the valencies of the heteroatoms. Furthermore, there is not any intention to be limited in any manner by the permissible substituents or organic compounds. Combinations of substituents and variables envisioned are preferably those that result in the formation of stable compounds useful in the production of polymeric materials.

General Description

The polymer industry is a fast-growing sector of the economy, and the next generation of biomass-derived polymers with new properties is needed. Polymers from monomers such as 2,5-furandicarboxylic acid are being explored as a reneweable replacement for PET-polyesters. In addition, there is a need for developing self-healing polymeric materials, which would enable enhanced durability and safety, as well as provide ecological benefits. Self-healing can occur through photochemical, Diels-Alder reactions, and non-covalent interactions like intermolecular hydrogen bonding and π-π stacking.

The molecular framework of furan has fascinated chemists for almost a century. The exclusive chemical nature of the furan moiety is attributed to its ability to resinify, which is an upshot of the aromatic-dienic duality of the molecule. Current polymerized compounds containing a furan moiety display this characteristic feature in the kinetic and mechanistic aspects of the polymerized material. The use of furan-based compounds as monomeric units for the creation of polyesters, polyamides, polyurethanes, and polyethers is highly desired in the industry as having the potential to create a renewable polymer feedstock. Presently, polyether, polyester, polycarbonates, and epoxy resins of significant commercial value are derived from non-renewable feedstock. Furfural can be accessed readily from renewable and non-food sources like corn husk, oat hulls, and sugarcane bagasse. The present disclosure demonstrates that the inexhaustible resource of furfural can be used to create a wide variety of polymeric materials.

The conversion of furfural to the furan-based monomer feedstock provides an opportunity to access many derivatives of the bis-furan (BF)-based moners, including the diisocyanate, diamine, diacid, and diacid chloride derivatives, which are depicted in FIG. 2 as compounds a-d, respectively. These derivatives have been used to generate polyurethanes, polyamides, polyurea, and polyesters. Provided herein are methods that utilize the derivatives bisfuran diamide (BFA) and bis-furan diol (BFD), depicted in FIG. 2 as compounds f and g, respectively, for the production of polymeric materials.

Currently, bis-furan-based polyesters are synthesized by reacting (1) diacid halide bis-furan with aliphatic or aromatic diols, or (2) diester bis-furan with glycol. Provided herein is a method of synthesizing polyester from a diol bearing a bis-furan monomer as a feedstock to build polyester, through reacting the feedstock with a diacid as a co-monomer via an alcohol esterification process. The synthesis is short, efficient, and can use recyclable glycerol in the first step. The resulting polyester can be cross-linked and in certain embodiments may exhibit self-healing properties.

As described in the examples herein, an assembly of bisfuran diol (BFD), also referred to as 5'-(propane-2,2-diyl)bis(furan-2,5-diyl)dimethanol (5), monomer was synthesized from commercial furfural over four synthetic steps. The BFD ($C_{13}H_{16}O_4$) crystallized in the monoclinic space group $P2_{1/c}$ with a=11.011(12) Å, b=10.443(12) Å, c=11.324(12) Å and an R value of 0.0358. Crystallographic analysis established molecular features involved in hydrogen bonding and packing of the BFD molecules. FIG. 7B illustrates a non-limiting example of a synthetic route for obtaining BFD. This synthesized BFD is useful as a feedstock for the production of bis-furan-based polymeric materials, such as the low molecular weight amorphous polyester (BFPE-1) described herein, which is accessed by reacting BFD with succinic acid.

Figure 30:
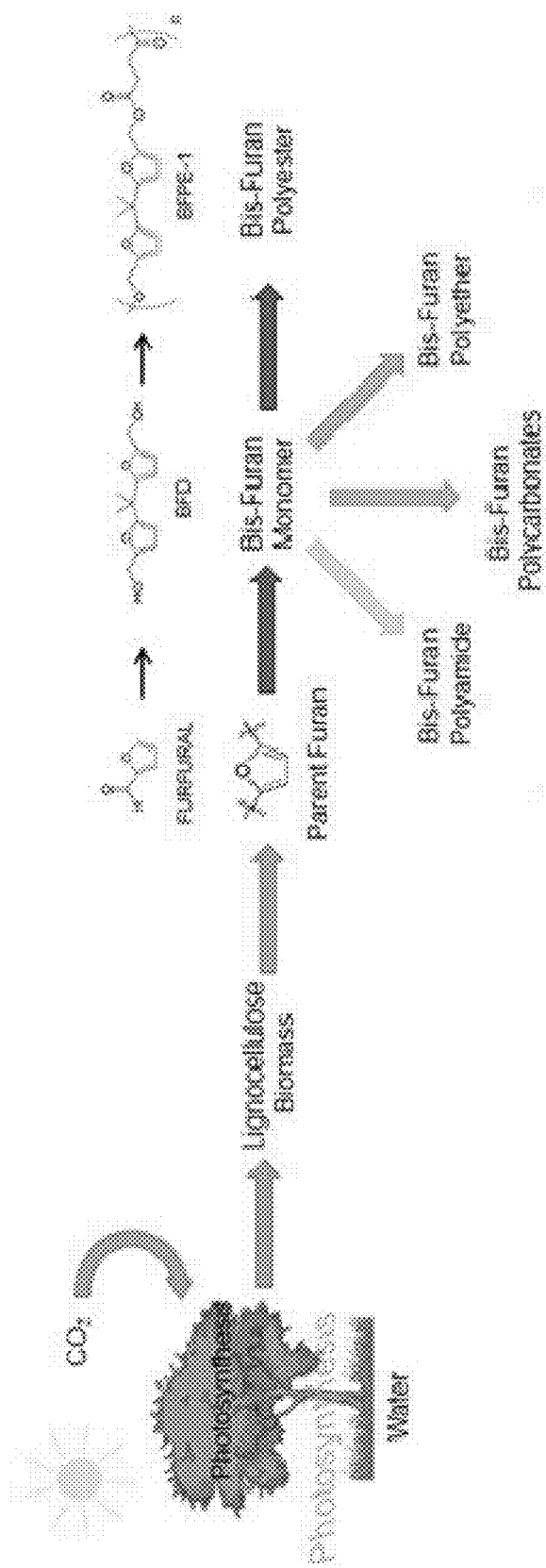
FIG. 30: Scheme showing the production of bis-furan-based polymeric materials from lignocellulosic biomass.

It is to be understood that the methods described herein can be utilized to produce a wide variety of polymeric materials including, but not limited to: polyesters, polyamides, polether, polycarbonates, and polyurethanes. The bis-furan polymeric materials described herein can be cross-linked, act as a thermoset or thermoplastic, and can possess self-healing properties. In certain embodiments, the bisfuran polymers can be worked, molded (i.e., injection-molded or blow-molded), extruded, or thermoformed, and are useful for the production of a wide variety of textiles, fabricated articles, and commodities such as, but not limited to: bottles, yarns, ropes, clothing, contains, trays, industrial fibres, films, liquid crystal displays, wood finishes, and insulating tapes. As shown in FIG. 30, the methods and compositions described herein can be utilized for the renewable production of useful bis-furan polymeric materials from lignocellulosic biomass.

Bis-Furan Polyester

Figure 29:
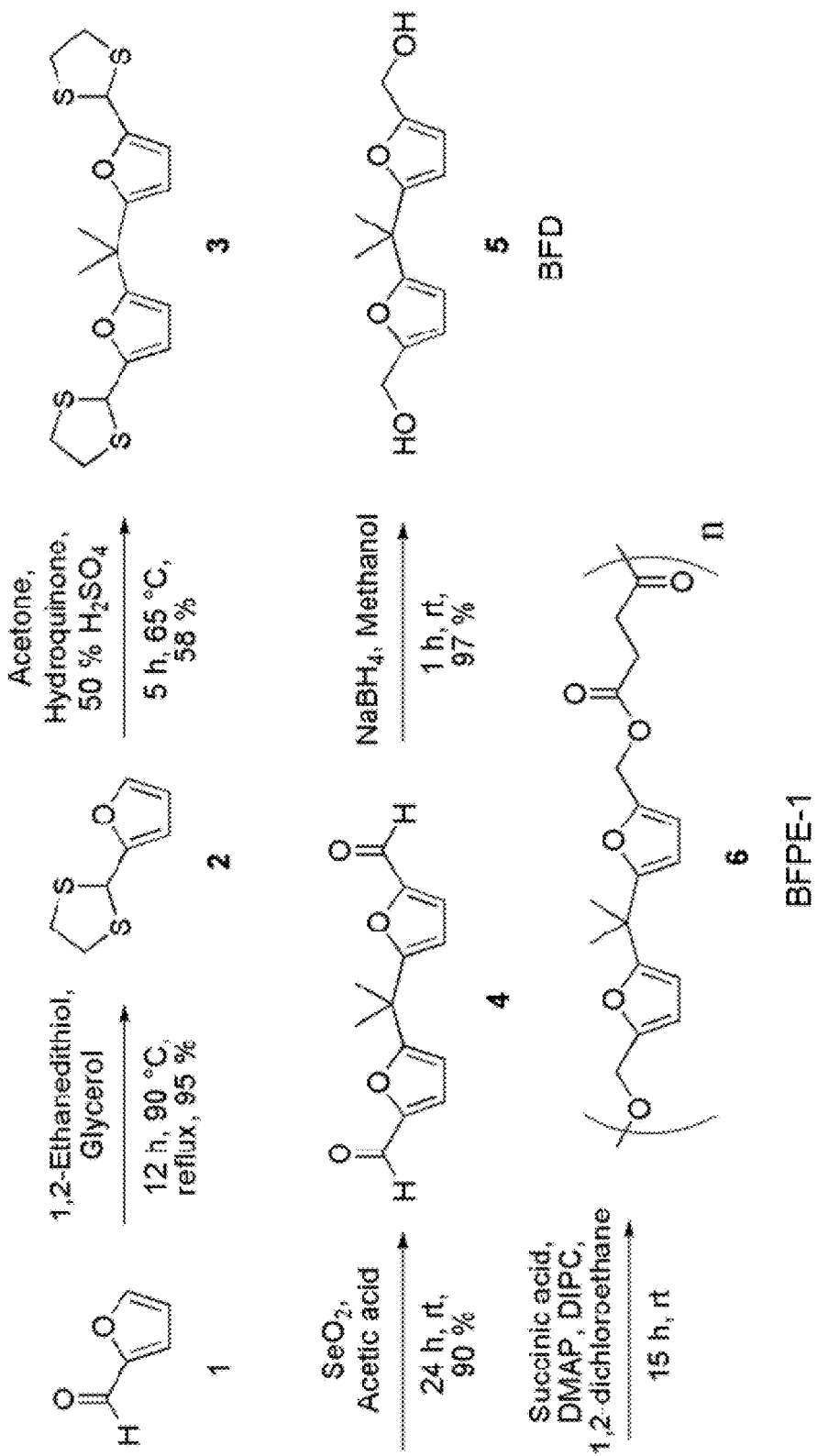
FIG. 29: Scheme showing a non-limiting example for the production of a bis-furan polyester from furfural.

Polyester is a class of polymer in which monomeric units are linked together with ester functionality. Synthetic polyester finds application as either thermoset or thermoplastic polymer segments based on the physical properties desired. Described herein is a bis-furan polyester (BFPE) synthesized from BFD via the reaction scheme shown in FIG. 3. Similarly, FIG. 29 shows a non-limiting example of a scheme for the synthesis of bis-furan polyester from furfural. The BFPE described herein has the general structural formula of Formula I:

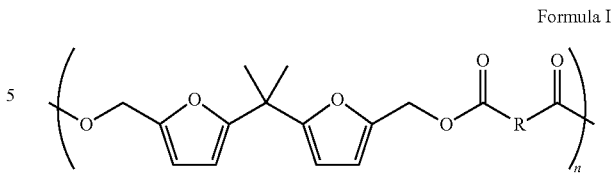

Formula I wherein R is $C_6H_4$ or $(CH_2)_x$, when x is from 1 to 10; and n is from 10 to 10,000.

Figure 3:
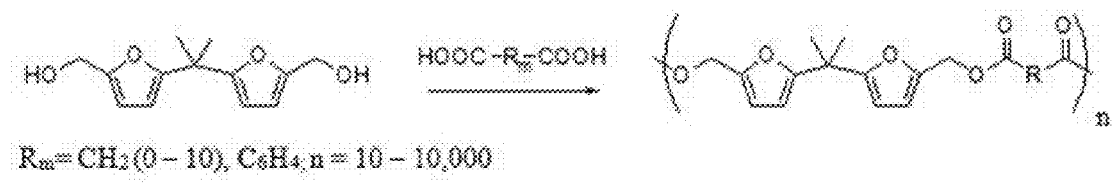
FIG. 3: Scheme showing the general reaction to produce bis-furan polyester (BFPE) from bisfuran diol (BFD).

As shown in FIG. 3, BFPE can be synthesized by reacting BFD with aliphatic or aromatic dicarboxylic acid reagents in the presence of carbodiimide to activate the acid. The reaction can be performed in the presence of a suitable nucleophilic catalyst such as, but not limited to, N,N-dimethyl-4-aminopyridine. Suitable dicarboxylic acid reagents include, but are not limited to: succinic acid, oxalic acid, malonic acid, glutaric acid, adipic acid, pimelic acid, suberic acid, azelaic acid, sebacic acid, undecanedioic acid, dodecanedioic acid, phthalic acid, isophthalic acid, terephthalic acid, maleic acid, glutaconic acid, traumatic acid, and muconic acid.

A wide variety of aliphatic or aromatic carbodiimides having the functional group —N=C=N— can be utilized to activate the acid. Suitable carbodiimides include, but are not limited to: N,N-diisopropylcarbodiimide; N,N'-diisopropylcarbodiimide; N,N-dicyclohexylcarbodiimide; dicyclohexylcarbodiimide; diisopropylcarbodiimide; dimethylcarbodiimide; diisobutylcarbodiimide; di-t-butylcarbodiimide; t-butylisopropylcarbodiimide; dioctylcarbodiimide; diphenylcarbodiimide; N,N'-bis(2-methylphenyl)carbodiimide; ethyl-3-(3-dimethylaminopropyl) carbodiimide; 1,3-bis(trimethylsilyl)carbodiimide; N-(tert-butyl)-N'-(2,6-dichlorophenyl)carbodiimide; N-(tert-butyl)-N'-(1-(2-chlorophenyl)-1-methylethyl)carbodiimide; and N-butyl-N'-(1-(2-chlorophenyl)-1-methylethyl)carbodiimide.

Figure 4:
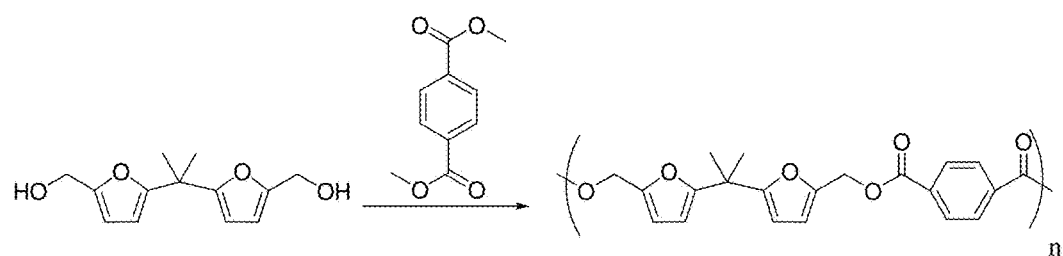
FIG. 4: Scheme showing the transesterification of BFD to access BFPE.

Alternatively, as shown in FIG. 4, BFPE can be generated by an alcohol transesterification reaction of the BFD with a diester-containing compound in the presence of either an acid or base catalyst. Suitable diester-containing compounds include, but are not limited to: phthalates (such as dimethyl terephthalate, monomethyl phthalate, dimethyl phthalate, diethyl phthalate, di-N-propyl phthalate, di-N-butyl phthalate, di-tert-butyl phthalate, diisobutyl phthalate, monoglycol esters of phthalic acid, diglycol esters of phthalic acid, di-N-octyl phthalate, diisooctyl phthalate, di-2-ethylhexyl phthalate, di-N-nonyl phthalate, diisononyl phthalate, di-N-decyl phthalate, diisodecyl phthalate, di-N-undecyl phthalate, diisododecyl phthalate, di-N-octadecyl phthalate, diisooctadecyl phthalate, di-N-eicosyl phthalate, monocyclohexyl phthalate, dicyclohexyl phthalate, di-isotridecylphthalate, or the like), adipates, azelates, sebacates, dodecanedioates, and dimerates. Suitable catalysts include, but are not limited to: mineral acids (such as sulfuric acid or sulfonic acid), metal hydroxides, metal oxides, metal alkoxides (such as aluminum isopropoxide, tetraalkoxytitanium, organotin alkoxides, or the like), non-ionic bases (such as amines, dimethylaminopyridine, guanidines, or the like), lipase enzymes, or a mixture of a Zn or Fe 1,3-dicarbonyl complex with an inorganic salt.

Figure 5:
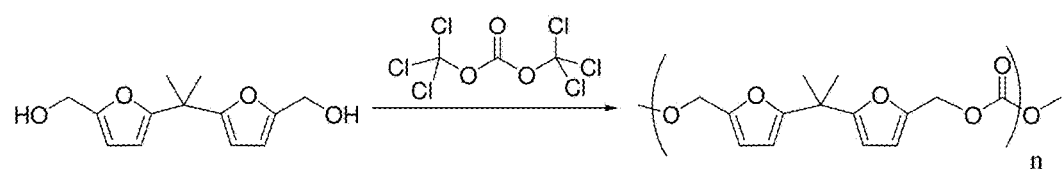
FIG. 5: Scheme showing the synthesis of bis-furan-based polycarbonate (BFPC) via phosgene.
Figure 6:
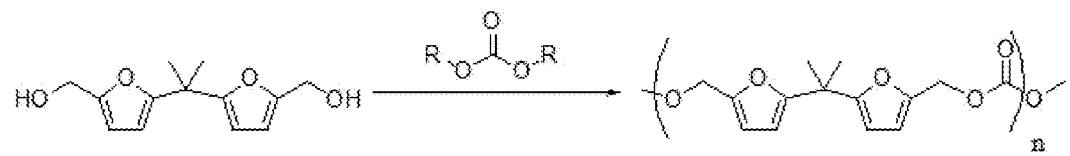
FIG. 6: Scheme showing the synthesis of BFPC via an alkyl carbonate ester.

In certain embodiments, the synthesized BFPE is an amorphous polyester with a low molecular weight ($M_n$=5 kDa). In some embodiments, the synthesis of BFPE uses a renewable diol rather than a renewable carboxylic acid. The synthesized BFPE is useful in a wide variety of applications, and can be utilized as a renewable and efficient replacement Bis-Furan Polycarbonate Polycarbonate is a class of polymer in which monomeric units are linked together with a carbonate group. Provided herein is bis-furan-based polycarbonate (BFPC), which can be synthesized by reacting BFD with triphosgene (or phosgene), in the presence of a base catalyst, as depicted in FIG. 5. Alternatively, as shown in FIG. 6, BFPC can be synthesized by reacting BFD with an aliphatic or aromatic carbonate ester reagent in the presence of a base catalyst. Suitable carbonate ester reagents include, but are not limited to: dimethyl carbonate, diethyl carbonate, diphenyl carbonate, ethylene carbonate, butylenes carbonate, propylene carbonate, trimethylene carbonate, or isopropyl carbonate. Suitable base catalysts include, but are not limited to: N,N-dimethyl formamide, sodium chloride, pyridine, or triethylamine.

The BFPC of the present disclosure has the general structural formula of Formula VI:

Formula VI

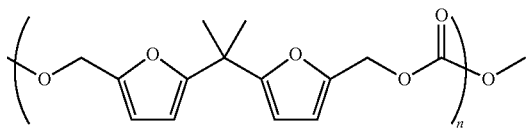

wherein n is from 10 to 10,000. The synthesized BFPC is useful in a wide variety of applications, and can be utilized as a renewable and efficient replacement for polycarbonates made from bisphenol A (BPA) monomers in many commodities. Additionally, the BFPC of the present disclosure may exhibit self-healing properties due to non-covalent interactions like hydrogen bonding and π-π stacking.

EXAMPLES

In the following examples, BFD was synthesized from commercially available furfural, employing minimal chemical transformations. The synthesized BFD compound was crystallized and the crystal structure was examined via X-ray crystallography to illucidate the molecular arrangement, hydrogen bonding, and packing of the crystalline monomer. This data was used to compare BFD with structurally related bisphenol A (BPA), and its known derivatives, to illucidate the estrogenic or anti-estrogenic activities in BFD. It was identified that the terminal hydroxyl groups in BFD are distinctively non-planar with the respective aromatic rings, thereby possibly hindering the binding of BFD to the estrogenic receptor. Additionally, the O—O distance between terminal hydroxyl groups of BFD was found to be 8.215(2) Å, which is substantially outside the range of xenoestrogens.

The synthesized BFD was utilized in a bench scale polyester polymerization using classical step-growth polymerization, which resulted in low molecular weight linear bis-furan polyester (BFPE) having an average molecular weight of 5 kDa, determined using a matrix-assisted laser desorption/ionization-time-of-flight/time-of-flight (MALDI-TOF/TOF) technique. Thermogravometric analysis (TGA), differential scanning calorimetry (DSC), dynamic light scattering (DLS) infrared spectroscopy (IR), $^1$H and $^{13}$C NMR were all performed to analyze the physical and structural characteristics of the synthesized polymer.

Materials and Methods

The starting material furfural and other fine chemicals were purchased from Acros Organics, and were used without further purification. All solvents were obtained from Fisher Scientific Co. and used without further purification. Silica (230-400 mesh) for flash column chromatography was obtained from Sorbent Technologies; precoated plates for thin-layer chromatography (TLC) were from E. Merck. TLCs (Silica Gel 60, $F_{254}$) were performed in specific developing solvents and visualized under UV. $^1$H and $^{13}$C spectra were recorded on INNOVA 600 and 150 MHz spectrometers, respectively, in $CDCl_3$ with residual $CHCl_3$ signal as an internal reference ($CDCl_3$: $^1$H NMR and $^{13}$CNMR at 7.27 ppm and 77.23 ppm, respectively). Low resolution mass spectra were obtained on an electrospray ioniziation mass spectrometer operated in the positive mode. IR spectra were recorded on a Perkin Elmer 1600 FTIR with wavelength range 4400 $cm^{-1}$ to 450 $cm^{-1}$.

Crystal data were collected at 110 K with a Bruker Apex Duo diffractomer (IUS microfocus source, CuKα=1.54178 nm) equipped with an Apex2 CCD detector and an Oxford Cryostream 700 low temperature device. A crystal with the dimensions 0.40×0.20×0.18 $mm^3$ was mounted on a 0.1 mm capillary with oil. Data were integrated using SAINT 7.68A; corrections for absorption and decay were applied using SADABS. A partial structure solution was obtained by direct methods in the space group $P2_1/c$, and remaining atoms were located with difference Fourier techniques. All non-hydrogen atoms were refined with anisotropic atomic displacement parameters; hydrogen atoms were refined with isotropic atomic displacement factors. All calculations were performed using SHELXS/SHELXL-97. All unique reflections were used in the refinement by full matrix least squares on $F^2$.

Dynamic light scattering experiments were conducted using Wyatt Technology Corporation—DynaPro Titan with the DynaPro Temperature—Controlled Microsampler. Samples of the BFPE-1 were prepared in THF with five dilutions—15.3 mg/ml, 7.65 mg/ml, 3.82 mg/ml, 1.91 mg/ml, and 0.95 mg/ml. In order to achieve high accuracy for the light scattering experiment all the dilutions were filtered to eliminate dust contamination using a 0.02 micron filter. 20.0 μl of each sample dilution was then subjected to dynamic light scattering at 100% laser power in a quartz cuvette held at 25.0° C. Five sets of repeat experiments were conducted for each dilution, with each set containing ten acquisitions requiring 20 seconds for individual acquisition.

Thermogravimetric analysis was performed using SDT 2960 simultaneous DTA-TGA, TA instrument with Universal V4.5A program. 11.1589 mg of BFPE-1 sample was subjected to weight change as a function of temperature under nitrogen flow of 110.0 ml/min by ramping up the temperature to 3° C./min from 0 to 800° C. Collected data points were analyzed for thermal stability and weight loss due to decomposition using Universal Analysis 2000, Version 4.5A, Build 4.5.0.5, TA instrument software.

DSC measurements were carried out using a Perkin Elmer Pyris Diamond Differential Scanning Calorimeter with an Intracooler, under nitrogen flow. The temperature and heat flow were calibrated using an indium standard. A heat-cool-reheat cycle was performed from −40° C. to 300° C., by ramping 10° C./min, quenching at 300° C./min, and a reheat cycle to record glass transition (T) between 15-25° C., and degradation temperature ($T_d$) of 260° C. After preliminary scans, 8.147 mg of the BFPE-1 sample was subjected to heat-cool-reheat cycle from −10° C. to 160° C., by ramping 5° C./min, cooling at 5° C./min, and a reheat cycle to record $T_g$=20° C., and $\Delta C_p$=0.676 J/g*° C.

Molecular weight determination spectra were acquired using ultraflexXtreme MALDI-TOF/TOF mass spectrometer from Bruker Daltonics. MALDI matrices used for analysis of the BFPE-1 were prepared using 2,5-dihyroxybenzoic acid (DHB) purchased from Sigma-Aldrich Co. A mixture, 1:1 (v/v) of the BFPE-1 and DHB solution in acetone, was mixed and deposited on the MALDI target plate and dried under vacuum. Interpretation of number average molecular weight ($M_n$), weight average molecular weight ($M_w$), polydispersity index (PDI), degree of polymerization (DP), repeat units, and fragmentation residue were all carried out using PolyTools software from Bruker Daltonics.

Example 1

Synthesis and Characterization of BFD

Figure 7A:
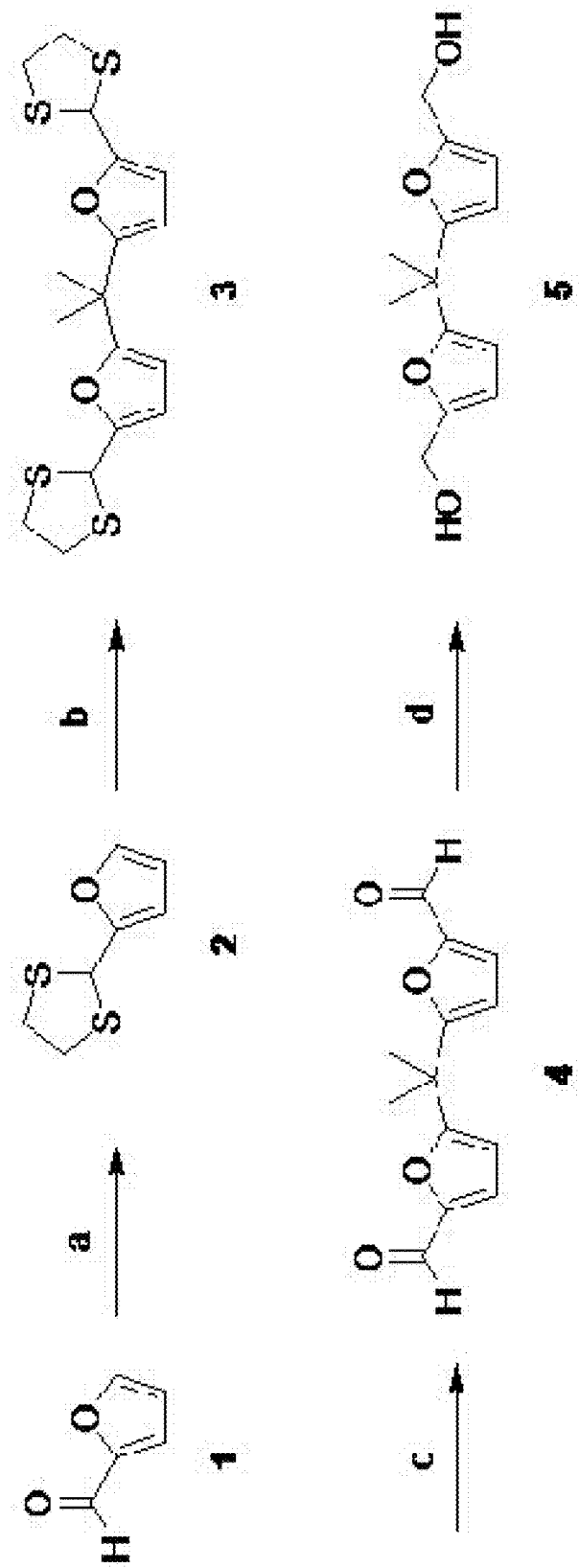
FIGS. 7A-7B: Schemes showing the synthetic rout to access BFD starting with furfural. Reagents and conditions in FIG. 7A: (a) 1,2-ethanedithiol, glycerol, 15 h, 90° C., 93%; (b) hydroquinone, acetone, aq. 50% H$_2$SO$_4$, 12 h, 65° C., 58%; (c) SeO$_2$, AcOH, 24 h, rt, 90%; and (d) NaBH$_4$, MeOH, N$_2$, 0.5 h, rt, 96%.
Figure 7B:
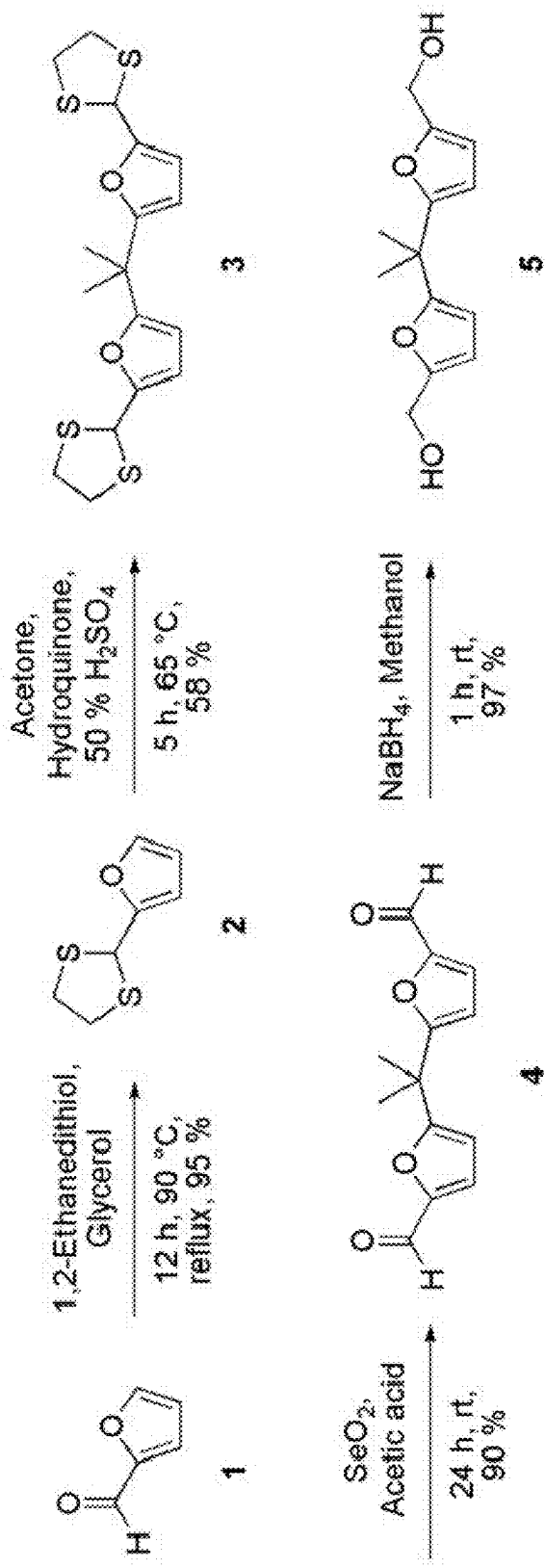

The scheme utilized to synthesize BFD is shown in FIGS. 7A-7B. BFD was designed as a monomer to undertake polymerization. Starting with commercially available furfural, protection of the aldehyde functionality was achieved as 1,3-dithiolane protected compound 2, by heating furfural along with 1,2-ethanedithiol in glycerol. Briefly, furfural (0.208 mol) was dissolved in glycerol (230 ml) at room temperature and 1,2-ethanedithiol (0.208 mol) was added to the reaction mixture. The reaction mixture was heated to 90° C. for a period of 15.0 hours. Completion of the reaction was monitored using TLC, a solvent system of hexanes:ethyl acetate (7:3). The reaction mixture was extracted with hexanes (3×100 ml) upon maximum conversion to the product. The organic layer was further washed with water, aqueous saturated sodium bicarbonate, and finally with brine. The organic layer was dried over anhydrous $MgSO_4$, and concentrated under reduced pressure. The crude material was further purified through fractional distillation (3.5 torr, 80-90° C.) to obtain light brown oil (33.3 g) with a 93% yield.

Compound 2 was subjected to Friedel-Crafts alkylation to yield compound 3. After several attempts, the optimal reaction condition was observed to be the entry 3 in Table 1 below, which resulted in the desired alkylation at C5 position of 1,3-dithiolane-protected furfural compound 2. Employing a catalytic amount of acid, acetone, and heating in a sealed acid digestion apparatus resulted in a 58% yield of compound 3.

TABLE 1

Friedel-Crafts Alkylation of Compound 2 with Acetone

| Entry | Acetone (equi.) | Catalyst | Temperature (° C.) | Time (hours) | Yield (%) |
|---|---|---|---|---|---|
| 1 | 0.5 | 95% $H_2SO_4$[a] | 10 | 16 | 16 |
| 2 | 3.8 | 95% $H_2SO_4$[b] | 65 | 3 | 33 |
| 3 | 3.8 | 95% $H_2SO_4$[c] | 65 | 3 | 58 |
| 4 | 3.8 | 95% $H_2SO_4$[c] | 125 | 3 | 37 |

[a]4M 2-(1,3-dithiolan-2-yl)furan with respect to 95% $H_2SO_4$.
[b]44 μl 50% $H_2SO_4$ (aq.)/g 2-(1,3-dithiolan-2-yl)furan.
[c]89 μl 50% $H_2SO_4$ (aq.)/g 2-(1,3-dithiolan-2-yl)furan.

Figure 19:
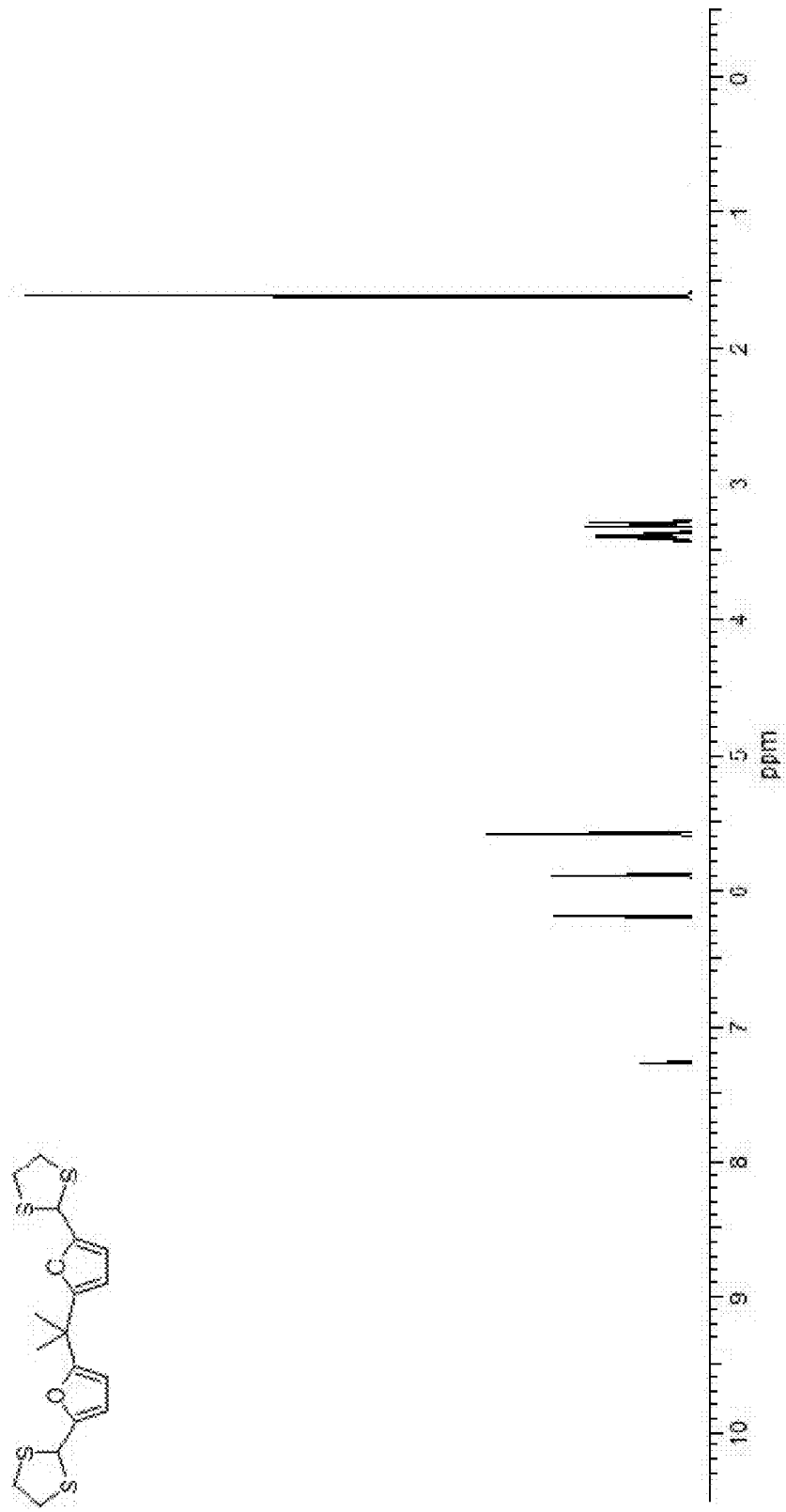
FIG. 19: $^1$H NMR spectrum of 5,5'-(propane-2,2'-diyl)bis [2-(1,3-dithuolan-2-yl)furan] (3).
Figure 20:
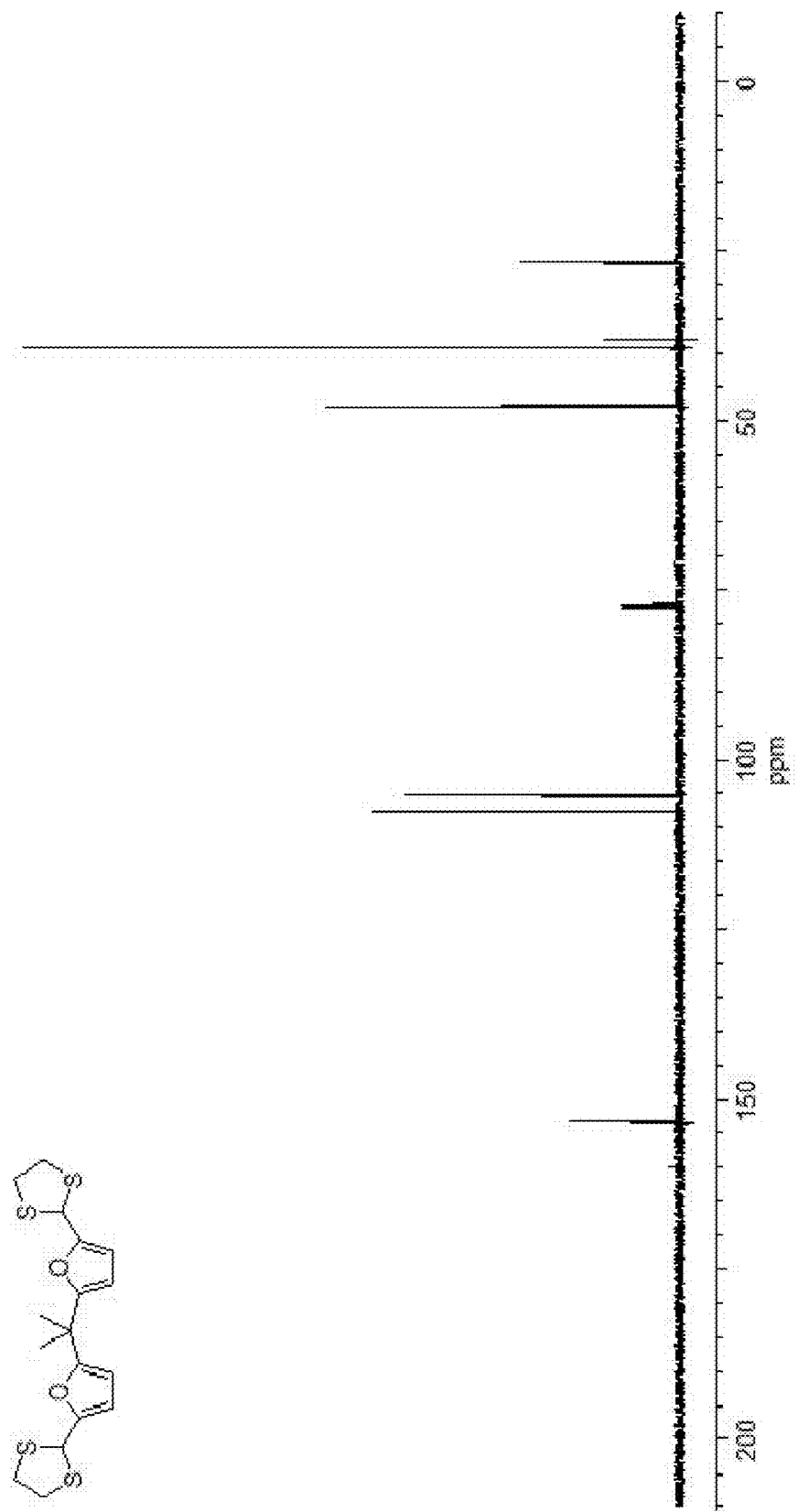
FIG. 20: $^{13}$C NMR spectrum of 5,5'-(propane-2,2'-diyl) bis[2-(1,3-dithuolan-2-yl)furan] (3).

Briefly, acetone (0.286 mol) was added to compound 2 (75.6 mmol) and stirred to dissolution at room temperature. Further hydroquinone (18.1 mmol) was also added to the reaction followed by dropwise addition of 50% $H_2SO_4$ (0.5 ml) while maintaining the temperature at 0° C. The reaction solution was further stirred for a period of 12.0 hours at 65° C. Completion of the reaction was monitored by TLC using hexanes:ethyl acetate (7:3) as a developing system. The reaction was diluted with water and neutralized with saturated aqueous sodium bicarbonate. The organic layer was then extracted with ether (3×100 ml). The organic layer was dried over anhydrous $MgSO_4$ and concentrated under reduced pressure. The crude material was further purified using silica gel column chromatography with 25% acetone in hexanes as an eluent to obtain pink-red crystals (16.8 g, 58%). $^1$H NMR (600 MHz, $CDCl_3$): δ 6.19 (d, 2H, J=3.0 Hz, furan ring), 5.89 (d, 2H, J=3.6 Hz, furan ring), 5.58 (s, 1H, dithio methylene), 3.39 (m, 4H, dithio ring), 3.29 (m, 4H, dithio ring), 1.61 (s, 6H, $CH_3$). $^{13}$C NMR (150 MHz, $CDCl_3$): δ 159.90, 153.23 (2C, aromatic), 107.43, 105.15 (2C, aromatic), 47.80 (2C, dithio ring carbon), 39.15 (1C, bridging carbon), 37.89 (4C, dithio ring carbon), 26.51 (2C, $CH_3$). HRMS: m/z [M+Na]$^+$ calcd for $C_{17}H_{30}O_2S_4$ is 407.5892. found 407.5. The $^1$H NMR and $^{13}$C NMR spectra of compound 3 are shown in FIG. 19 and FIG. 20, respectively.

Figure 21:
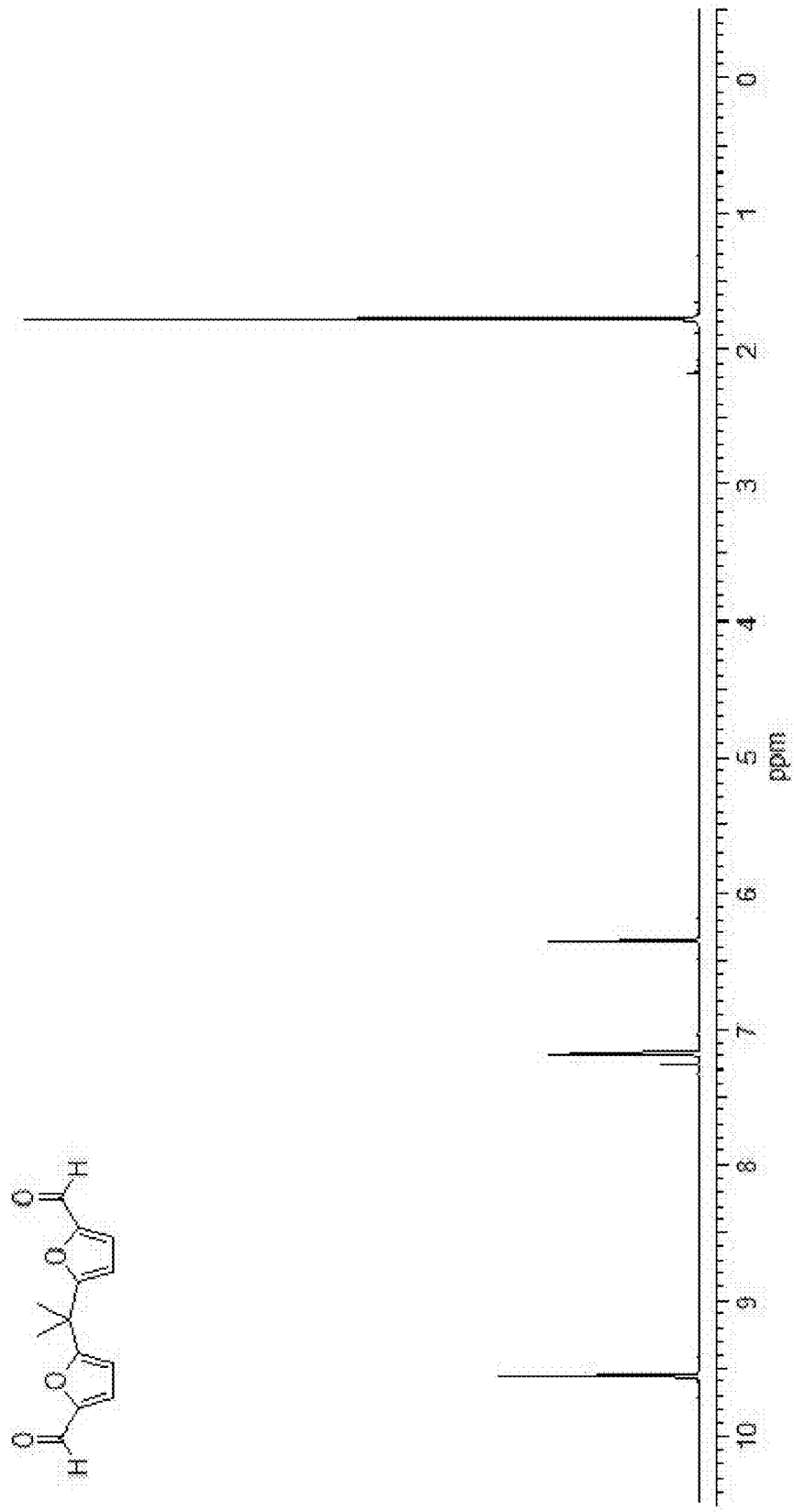
FIG. 21: $^1$H NMR spectrum of 5,5'-(propane-2,2'-diyl) difuran-2-carbaldehyde (4).
Figure 22:
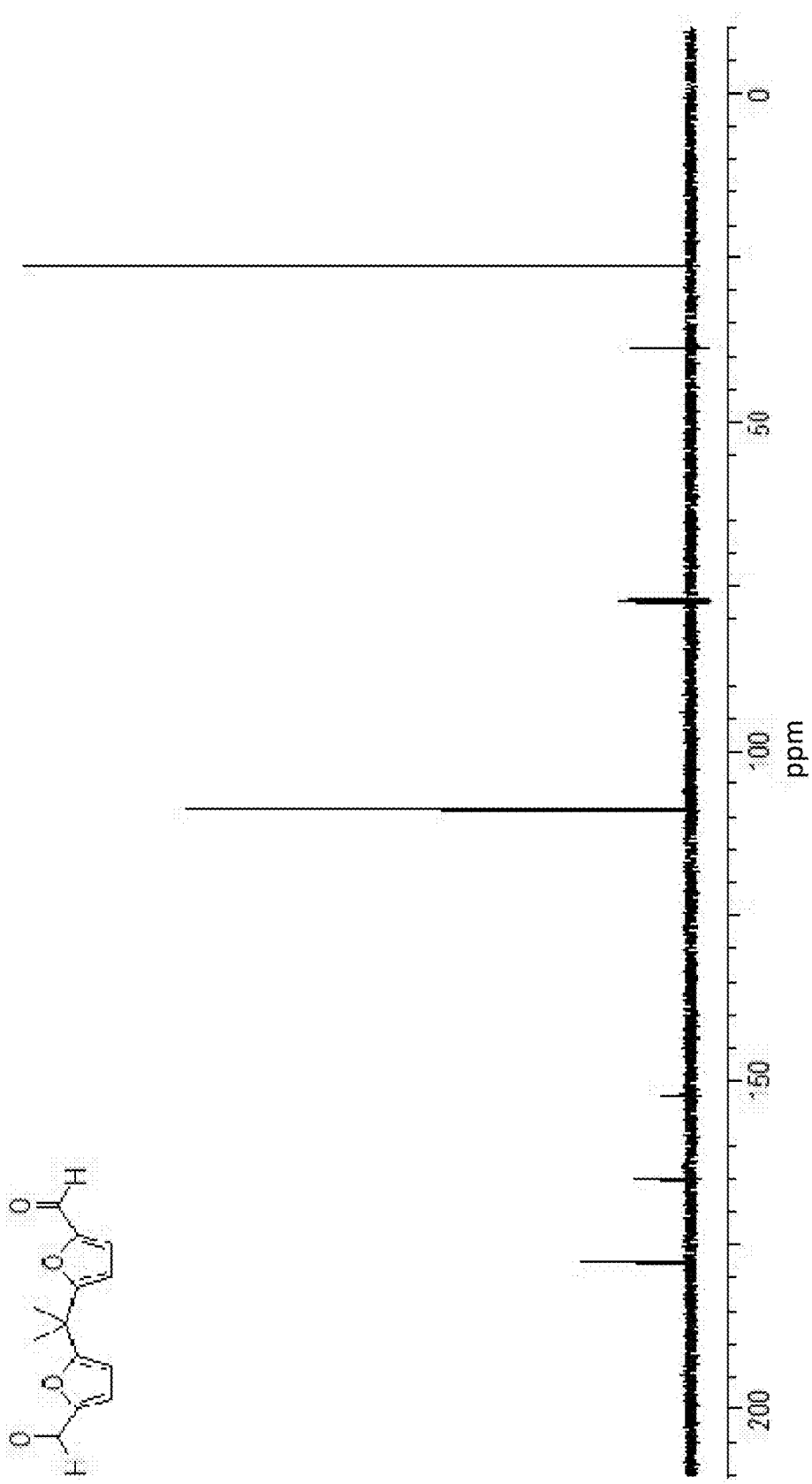
FIG. 22: $^{13}$C NMR spectrum of 5,5'-(propane-2,2'-diyl) difuran-2-carbaldehyde (4).

The dedithioacetalization was carried out using selenium (IV) oxide ($SeO_2$) and with acetic acid (AcOH) as the solvent. Employing 5 eq. of $SeO_2$ per 1,3-dithiolane protecting group led to desired deprotected dialdehyde 4 in 90% isolated yield. Briefly, dithiolane compound 3 (0.52 mmol) was dissolved in acetic acid (5 ml) and stirred to dissolution at room temperature. Selenium oxide (2.6 mmol) was added to the reaction mixture and stirred further for a period of 24 h at room temperature. Reaction progress was monitored with TLC using hexanes:acetone (7:3) for development. The reaction was filtered and concentrated under reduced pressure to obtain a viscous oil. The product was taken up in diethyl ether and washed with aqueous saturated sodium bicarbonate (10 ml). The organic layer was dried over anhydrous $MgSO_4$ and concentrated under reduced pressure to obtain a pinkish-red semi-solid crude material. The compound was further purified using silica gel column chromatography, solvent system 30% acetone in hexanes to obtain a pale yellow solid (108 mg, 90%). $^1$H NMR (600 MHz, $CDCl_3$): δ 9.55 (s, 2H, aldehyde H), 7.18 (d, 2H, J=3.6 Hz, aromatic), 6.34 (s, 2H, J=3.6 Hz, aromatic), 1.77 (s, 6H, methyl —$CH_3$). $^{13}$C NMR (150 MHz, $CDCl_3$): δ 177.61 (2C, carbonyl), 164.93-108.61 (8C, aromatic), 38.69 (1C, bridging carbon), 25.99 (2C, methyl). HRMS: m/z [M+Na]$^+$ calcd for $C_{13}H_{12}O_4$ is 255.22175. found 255.4. The $^1$H NMR and $^{13}$C NMR spectra of compound 4 are shown in FIG. 21 and FIG. 22, respectively.

Figure 23:
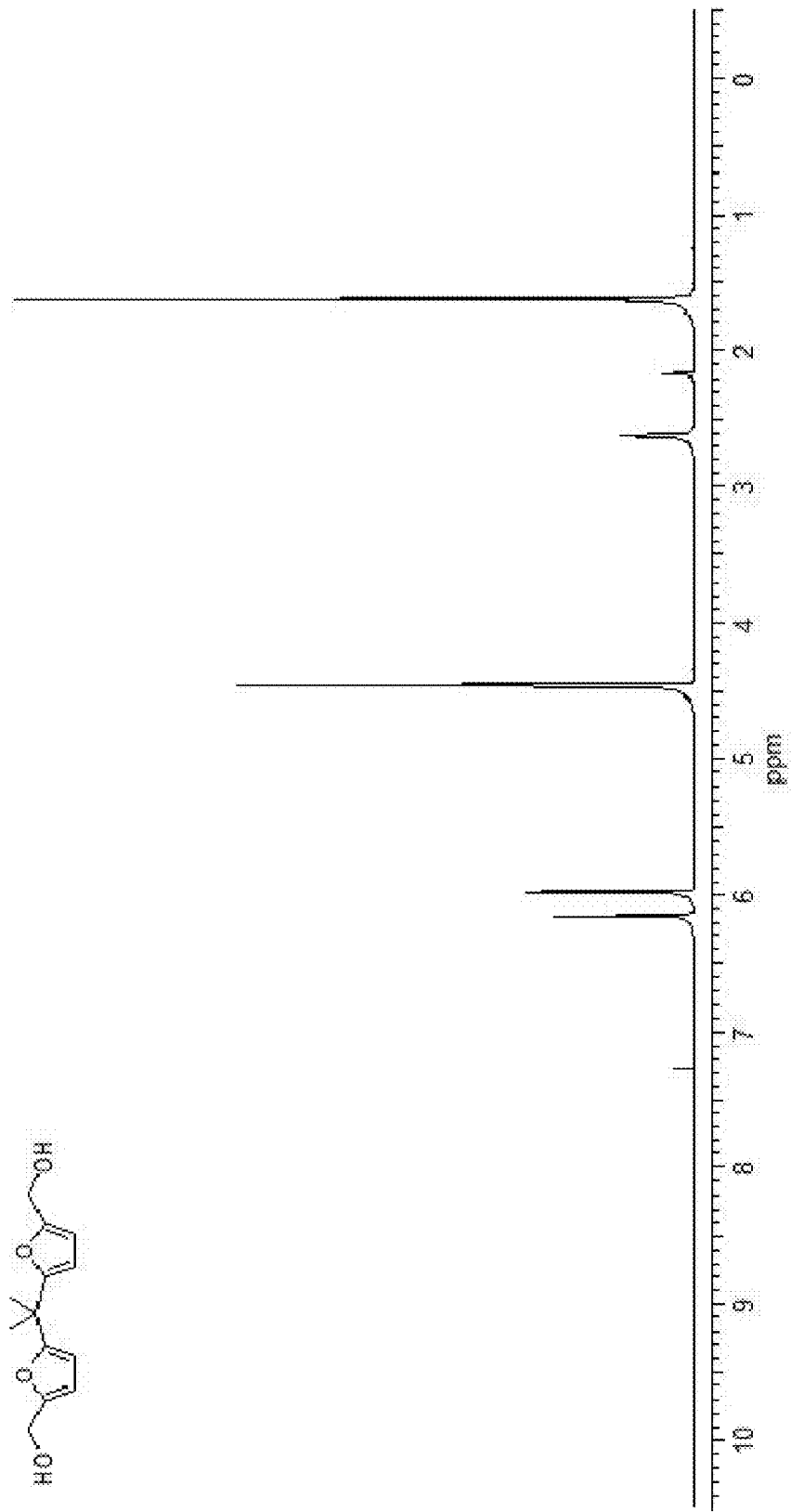
FIG. 23: $^1$H NMR spectrum of BFD (5).
Figure 24:
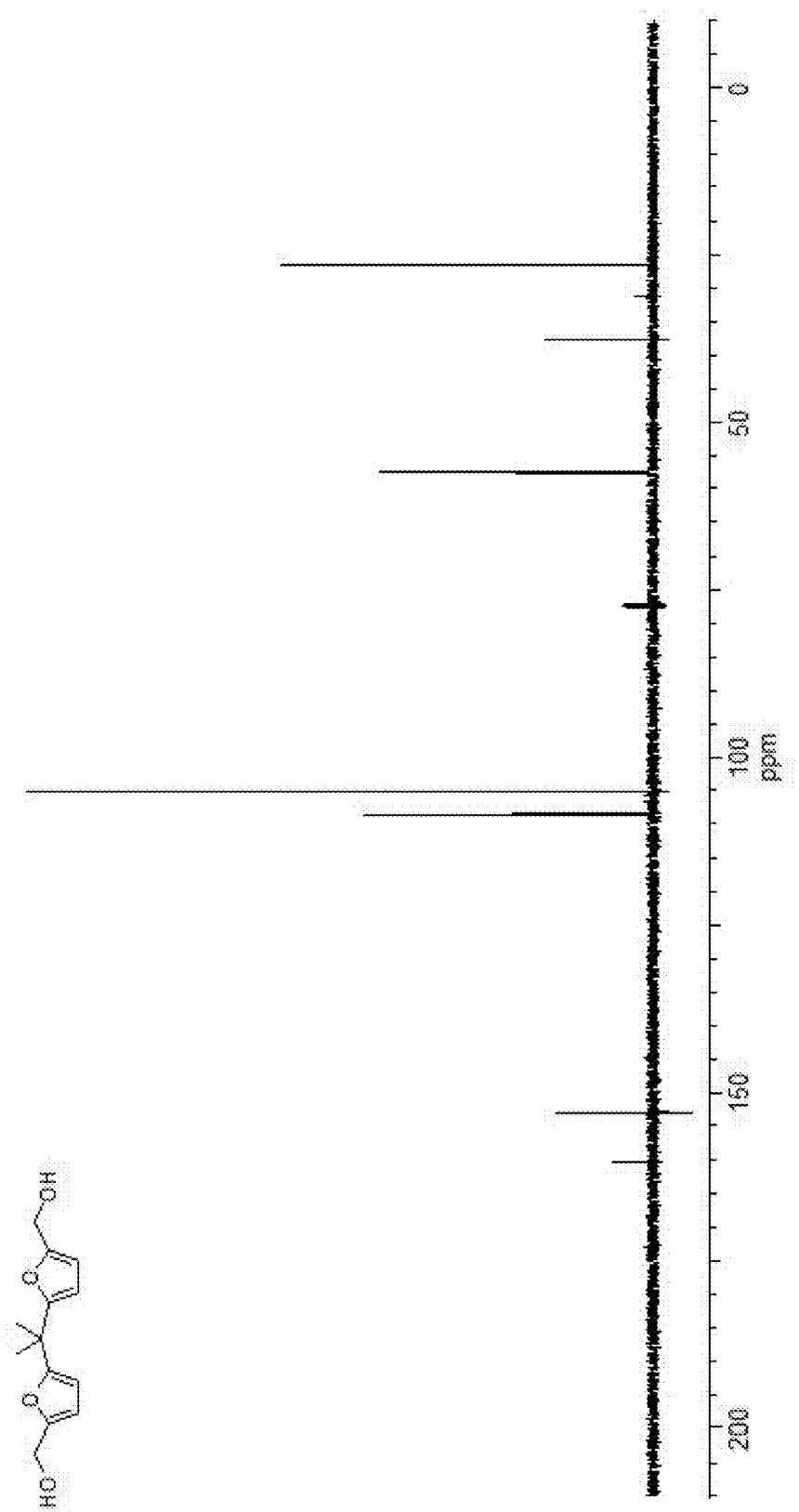
FIG. 24: $^{13}$C NMR spectrum of BFD (5).
Figure 25:
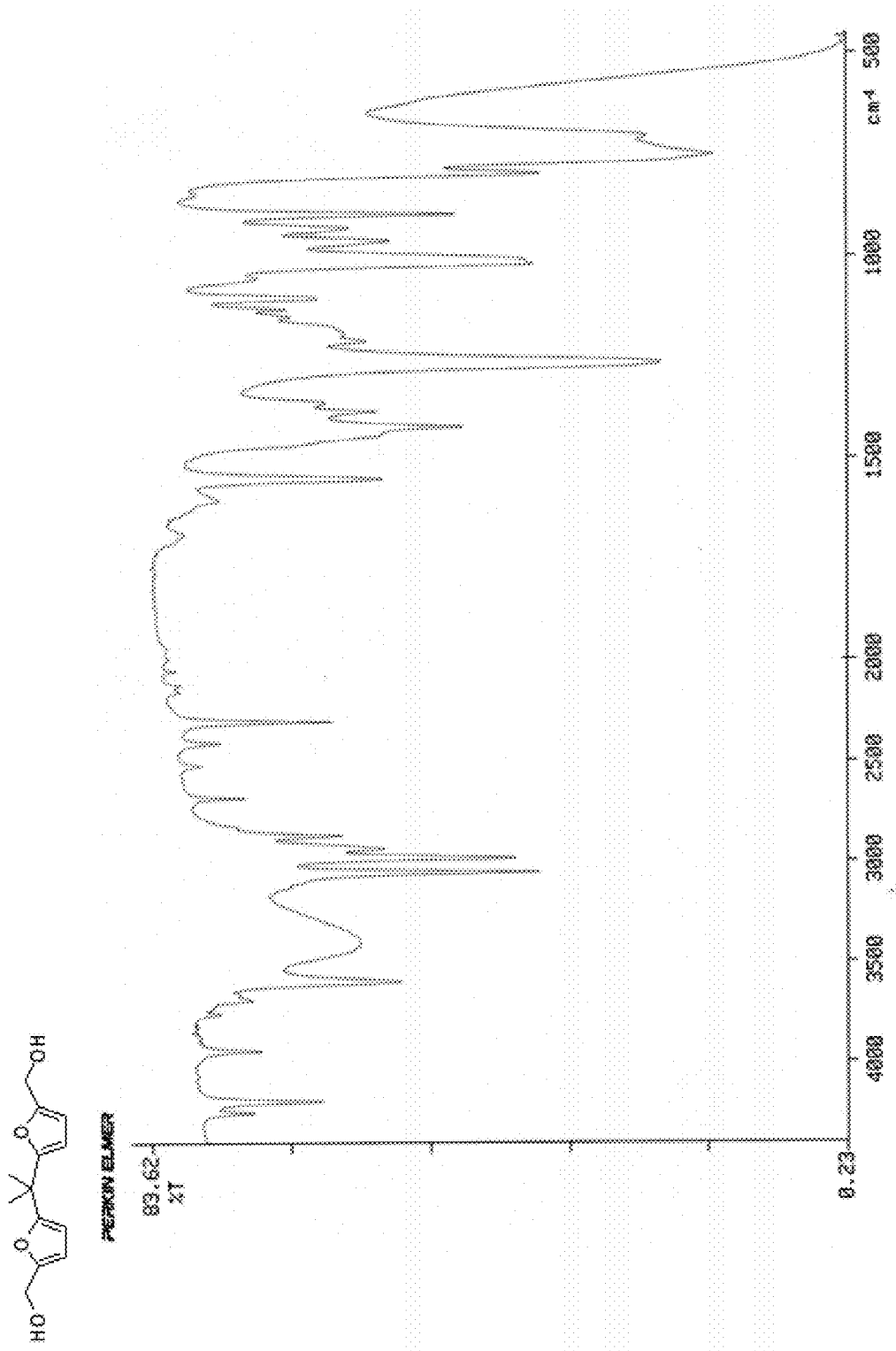
FIG. 25: IR spectrum of BFD (5).

The reduction of dialdehyde 4 to access BFD was accomplished using sodium borohydride ($NaBH_4$) in methanol. The aldehyde groups were reduced using 4.0 equivalents of $NaBH_4$ to afford compound 5. Briefly, dialdehyde 4 (0.30 mmol) was dissolved in methanol (2.0 ml) under $N_2$ atmosphere. After dissolution, sodium borohydride (1.2 mmol) was slowly added to the solution. The suspension was stirred for 40 minutes and the reaction was monitored using TLC. The TLC was developed with hexanes:acetone (7:3). The reaction was quenched with water (10 ml) and extracted with ethyl acetate. The organic layer was dried over anhydrous $MgSO_4$ and concentrated under reduced pressure to obtain oily crude material. The compound was purified using silica gel chromatography with 30% acetone in hexanes as an eluent to obtain a light yellow solid (68 mg, 96%). $^1$H NMR (600 MHz, $CDCl_3$): δ 6.14 (d, J=3.0 Hz, 2H, aromatic), 5.97 (d, J=3.0 Hz, 2H, aromatic), 4.59 (s, 4H, methylene —$CH_2$), 2.62 (s, 2H, hydroxyl —OH), 1.62 (s, 6H, methyl —CH$_3$). $^{13}$C NMR (150 MHz, CDCl$_3$): δ 160.12-105.00 (8C, aromatic), 57.44 (2C, methylene), 37.54 (1C, bridging carbon), 26.42 (2C, methyl). HRMS: m/z [M+Na]$^+$ calcd for C$_{13}$H$_{16}$O$_4$ is 259.2535. found 259.4. FTIR (NaCl, cm$^{-1}$): 3400, —OH, broad. The $^1$H NMR and $^{13}$C NMR spectra of compound 5 are shown in FIG. 23 and FIG. 24, respectively, and the IR spectrum of compound 5 is shown in FIG. 25.

Figure 8:
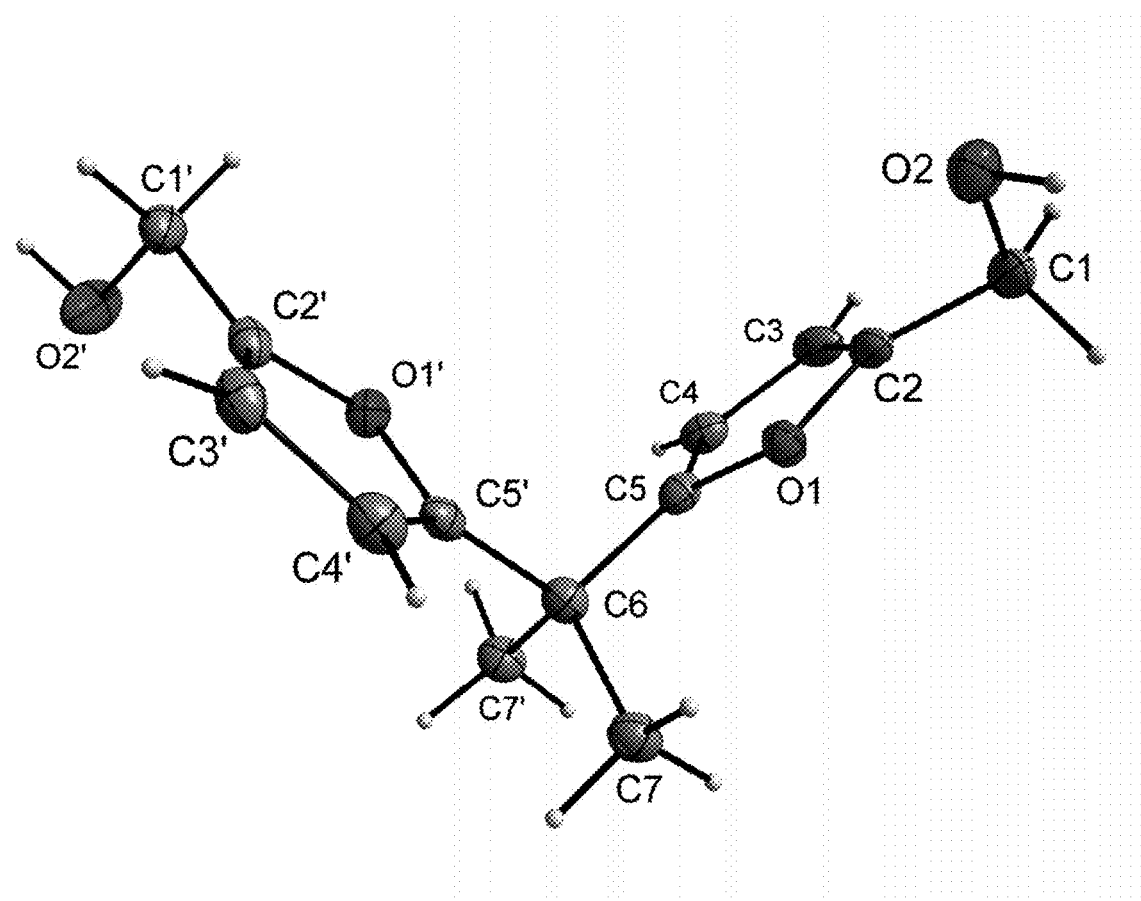
FIG. 8: Oak Ridge Thermal Ellipsoide Plot (ORTEP) drawing of BFD with 50% probability ellipsoids and labeling scheme.

Crystallographic analysis of the BFD revealed several things. Molecules of the BFD compound 5, which has the IUPAC name 5,5'-(propane-2,2-diyl)bis(furan-2,5-diyl)dimethanol, crystallized in the space group P2$_{1/c}$ with one molecule in the asymmetric unit. As illustrated in FIG. 8, the molecules exhibit an appropriate non-crysallographic 2-fold symmetry through the central bridging C6 atom with the oxygen-atoms O, O1' and O2, O2' pointing in opposite directions, respectively. The orientation of the two aromatic rings towards each other can be described by the dihedral angle between the mean planes of the two rings, which has a value of 80.15(5)°.

The conformation of the BFD molecules can be visualized as a propeller-like arrangement of the aromatic rings. A pitch angle, ψ, can be used to describe the amount of rotation around the C6-C5 or C6-C5' bond, turning the respective aromatic ring in (ψ=0°) and out of the central C5-C6-C5' plane. The two rings in BFD have pitch angles of 74.98(8°) and 66.04(7)°.

The hydroxyl groups as —CH$_2$OH in BFD are distinctively non-planar with O2 and O2' being 1.050(3) Å and 1.210(3) Å above the respective aromatic ring moiety. The O—O distance between terminal hydroxyl groups of BFD has a value of 8.215(2) Å.

Further influence to the overall conformation of these molecules in the solid state structures comes from steric hindrance of the two methyl groups (C7 and C7') and packing effects, especially hydrogen bonds. Although on initial inspection, molecules of BFD seem to exhibit a non-crystallographic 2-fold axis, closer examination reveals a quite different secondary coordination sphere for O1 and O1', as well as O2 and O2'. While the furan oxygen O1 is not involved in any hydrogen bonds, the other furan oxygen, O1', acts as an acceptor with O1' . . . H2-O2 (x, 0.5−y, 0.5+z)=2.05(3)Å. Concomitantly, the C2-O1 and C5-O1 bonds are 1.380(2) Å and 1.378(2) Å shorter than the comparable C2'-O1' and C5'-O1' bonds of 1.386(2) Å, respectively.

In a similar way, the hydroxyl group O2'-H2' acts as a hydrogen bond donor O2'-H2' . . . O2(−x, 2−y, 1−z)=1.90(3) Å, while the other hydroxyl group O2-H2 acts simultaneously as a hydrogen-bond acceptor (O2 . . . H2'-O2'(−x, 2−y, 1−z)=1.90(3) Å) and as a hydrogen-bond donor to a furan oxygen (O2-H2 . . . O1' (x, 1.5−y, −0.5+z)=2.05(3) Å).

Figure 9:
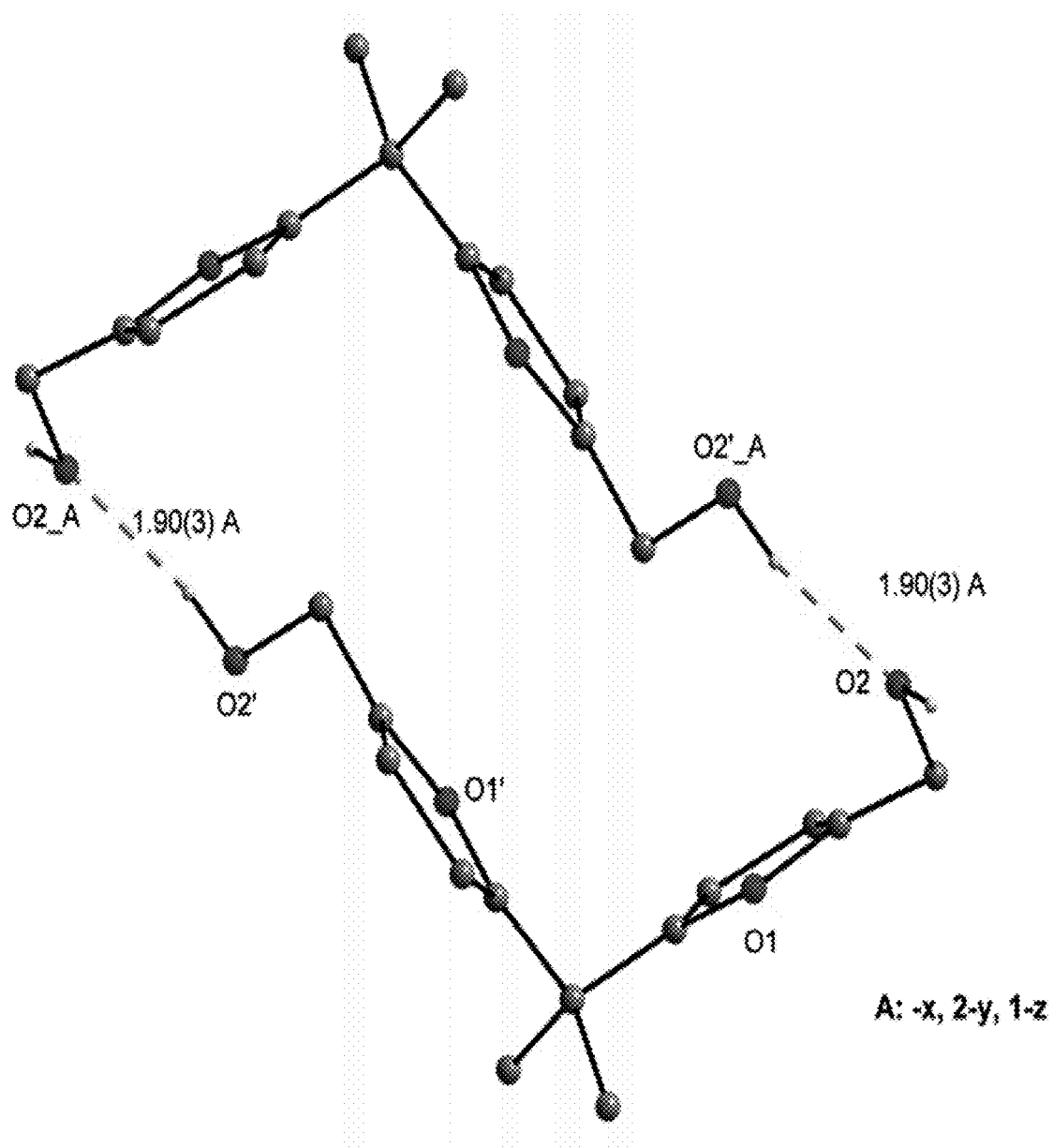
FIG. 9: Dimer of BFD created by strong H-bonds.
Figure 10:
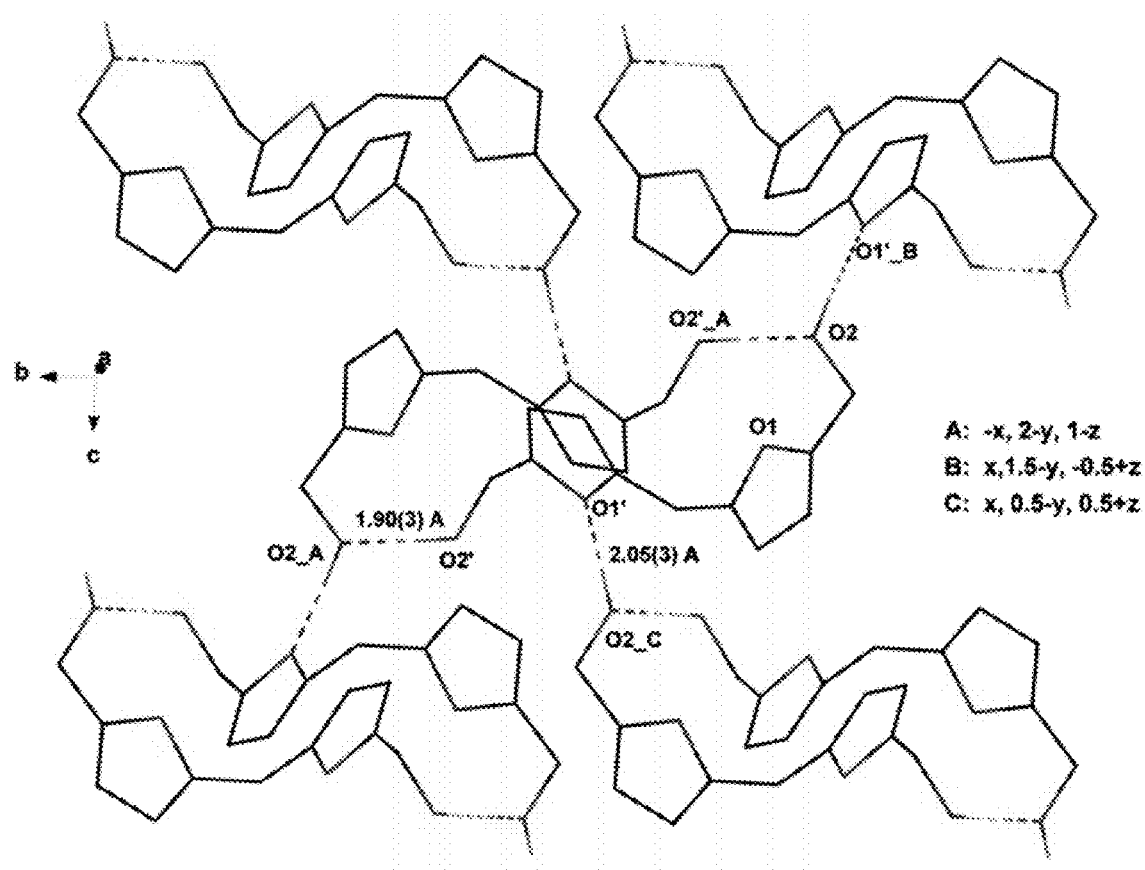
FIG. 10: Plane of H-bonded BFD dimers. H-atoms not involved in the H-bonding scheme and methyl-C-atoms are omitted for clarity.
Figure 11:
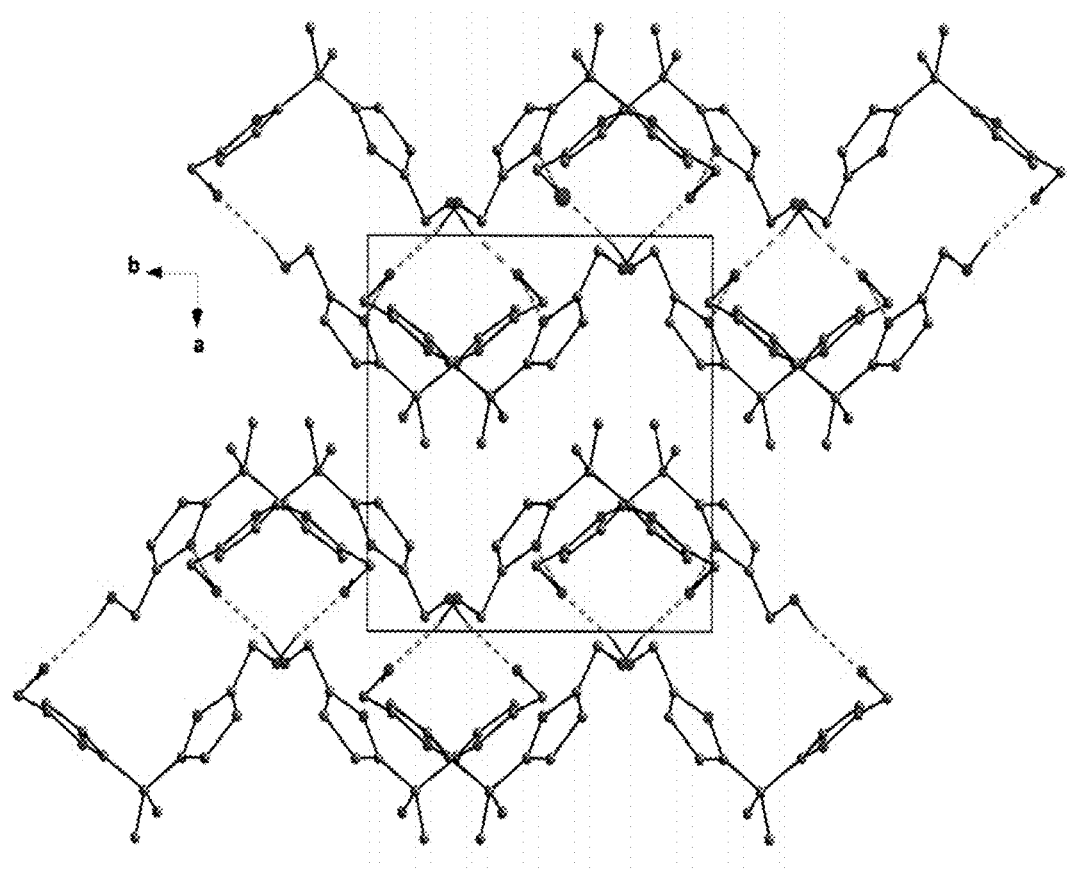
FIG. 11: Packing diagram of BFD onto the ab plane.

FIG. 9 shows hydrogen bonds between two molecules of BFD with O2' as a hydrogen bond donor and O2 as the acceptor forming a rectangular dimer of approximate dimensions 8×12 Å. The O2-H2 group is further involved in a weaker hydrogen bond, acting as a hydrogen bond donor to the furan oxygen O1'. This slightly longer H-bond connects each dimer to two other dimers above, and two more below, the central ring, resulting in H-bonded planes of dimers parallel to the bc-plane. This is illustrated in FIG. 10, where hydrogen atoms not involved in the H-bonding scheme and methyl-C-atoms have been omitted for clarity. Within each plane, the dimers are arranged in a zigzag pattern, with the planes being separated by a hydrophobic surface built by the CH$_3$ groups, as shown in FIG. 11. Details of the crystal data and structure refinement for BFD are tabulated in Table 2, below.

TABLE 2

| Crystal Data and Structure Refinement for BFD | |
|---|---|
| Crystal system | Monoclinic |
| Formula | C$_{13}$H$_{16}$O$_4$ |
| Formula weight | 236.26 |
| Space group | P2$_1$/c |
| a | 11.0113(12) Å |
| b | 10.4428(12) Å |
| c | 11.3244(12) Å |
| β | 115.992(5) |
| V | 1170.5(2) Å$^3$ |
| Z | 4 |
| Temperature | 110(2) K |
| Wavelength | 1.54178 Å |
| Density | 1.341 Mg/m$^3$ |
| Absorption coefficient | 0.819 mm$^{-1}$ |
| F(000) | 504 |
| Crystal size | 0.40 × 0.20 × 0.18 mm$^3$ |
| θ range | 6.07 to 59.31° |
| Reflections collected | 10292 |
| Independent reflections | 1657 [R(int) = 0.0510] |
| Max., Min. transmission | 0.8667 and 0.7354 |
| Refinement method | Full-matrix least-squares on F$^2$ |
| Data/restraints/parameters | 1657/0/218 |
| Goodness-of-fit on F$^2$ | 1.056 |
| Final R indices [I > 2sigma(I)] | R$_1$ = 0.0352, wR$_2$ = 0.0915 |
| R indices (all data) | R$_1$ = 0.0358, wR$_2$ = 0.0921 |
| Largest diff. peak and hole | 0.218 and −0.236 e.Å$^{-3}$ |

The crystal structure of BFD was compared with BPA and its derivatives. BPA is a ubiquitous molecule in the polymer industry known to exhibit estrogenic activity. The dihedral angle between the two aromatic rings of BFD has a value (80.15(5)°) that is within the broad range of equivalent angles in the solid state structures of BPA and its derivatives (71.43°-89.62°). Specifically, the three crystallographically independent molecules in the crystal structure of BPA possess dihedral angles of 79.7(2)°, 83.6(2)°, and 86.9(2)°. However, there is a significant difference in the conformation of the BPA and BFD structures with respect to the propeller-like arrangement of the aromatic rings. A pitch angle, ψ, can be used to describe the amount of rotation around the C6-C5 or C6-C5' bond, turning the respective aromatic ring in (ψ=0°) and out of the central C5-C6-C5' plane. The two rings in BFD have pitch angles of 74.98(8)° and 66.04(7)°, which means they are significantly more twisted toward a perpendicular arrangement than the ones in all three BPA molecules, whose pitch angles range from only 45.59(6)° to 59.62(7)°.

The binding of BPA to human estrogen-related receptor γ (ERRγ), as well as its activity as an endocrine disruptor, has been previously established. Furthermore, estrogen receptor ligands possessing hydroxyl groups with O—O distances ranging from 9.7-12.3 Å typically display a medium to strong endocrine receptor ligand capacity, and ligands with O—O distances outside of this range generally weakly interact with the receptor. The O—O distance between the oxygen atoms of BPA is 9.404 Å. Without wishing to be bound by theory, it is believed that the planarity of the non-hydrogen atoms of the hydroxyphenol moieties in BPA is advantageous for its locking into the estrogen acceptor pocket of ERRγ. By replacing the hydroxyl group with a CH$_2$OH group in BFD, the geometry of the substituent is distinctively non-planar with O2 and O2', being 1.050(3) Å and 1.210(3) Å above the respective aromatic ring moiety. Without wishing to be bound by theory, it is believed this hinders the binding of BFD to the receptor. Also, the O—O distance between terminal hydroxyl groups of BFD is 8.215 (2) Å, which is substantially outside the range of xenoestrogens.

Example 2

Synthesis and Characterization of Poly (Furan Succinate) Copolyester (BFPE-1)

Figure 12:
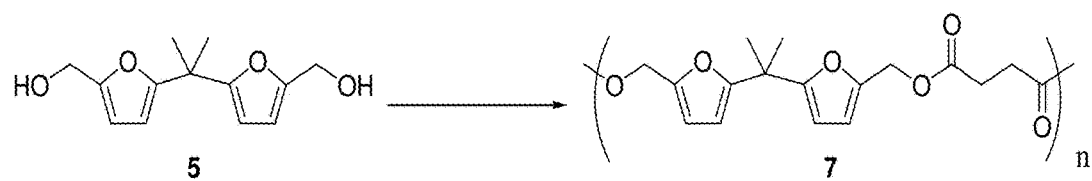
FIG. 12: Scheme showing the synthesis of BFPE-1 (7) starting with BFD (5). Reagents and conditions used: succinic acid, N,N-dimethyl-4-aminopyridine, N,N'-diisopropylcarbodiimide, 1,2-dicholoroethane, N$_2$, 15.0 h, rt.

Bifunctional monomers yield linear polymeric chains to generate similar linear polyester. In this example, a step-growth polymerization using two co-monomeric units was performed. Succinic acid was the dicarboxylic acid used as the second monomeric unit to evaluate the polyester polymerization via alcohol esterification. The reaction scheme utilized in this example is shown in FIG. 12.

Figure 26:
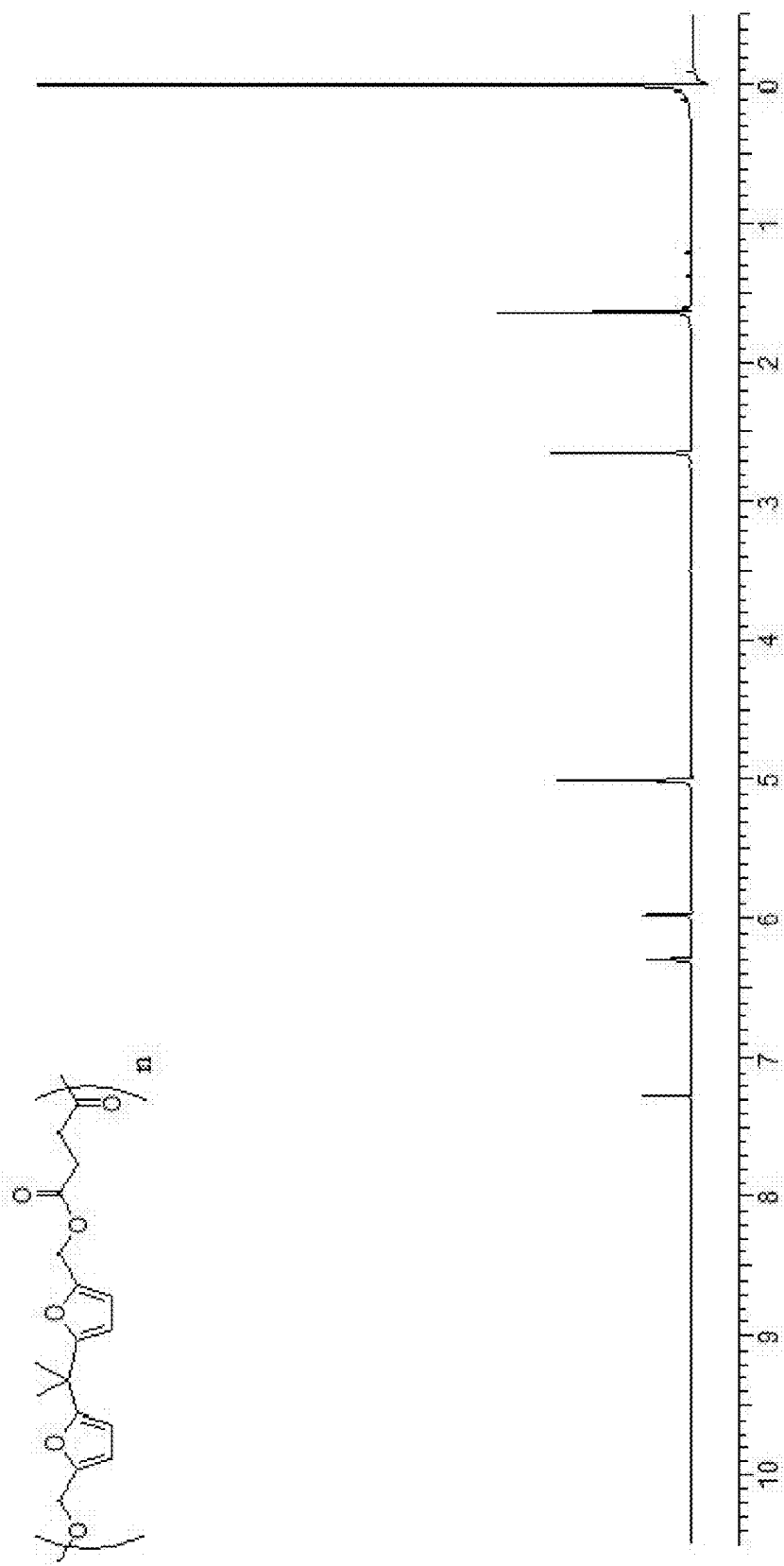
FIG. 26: $^1$H NMR spectrum of BFPE-1 (7).
Figure 27:
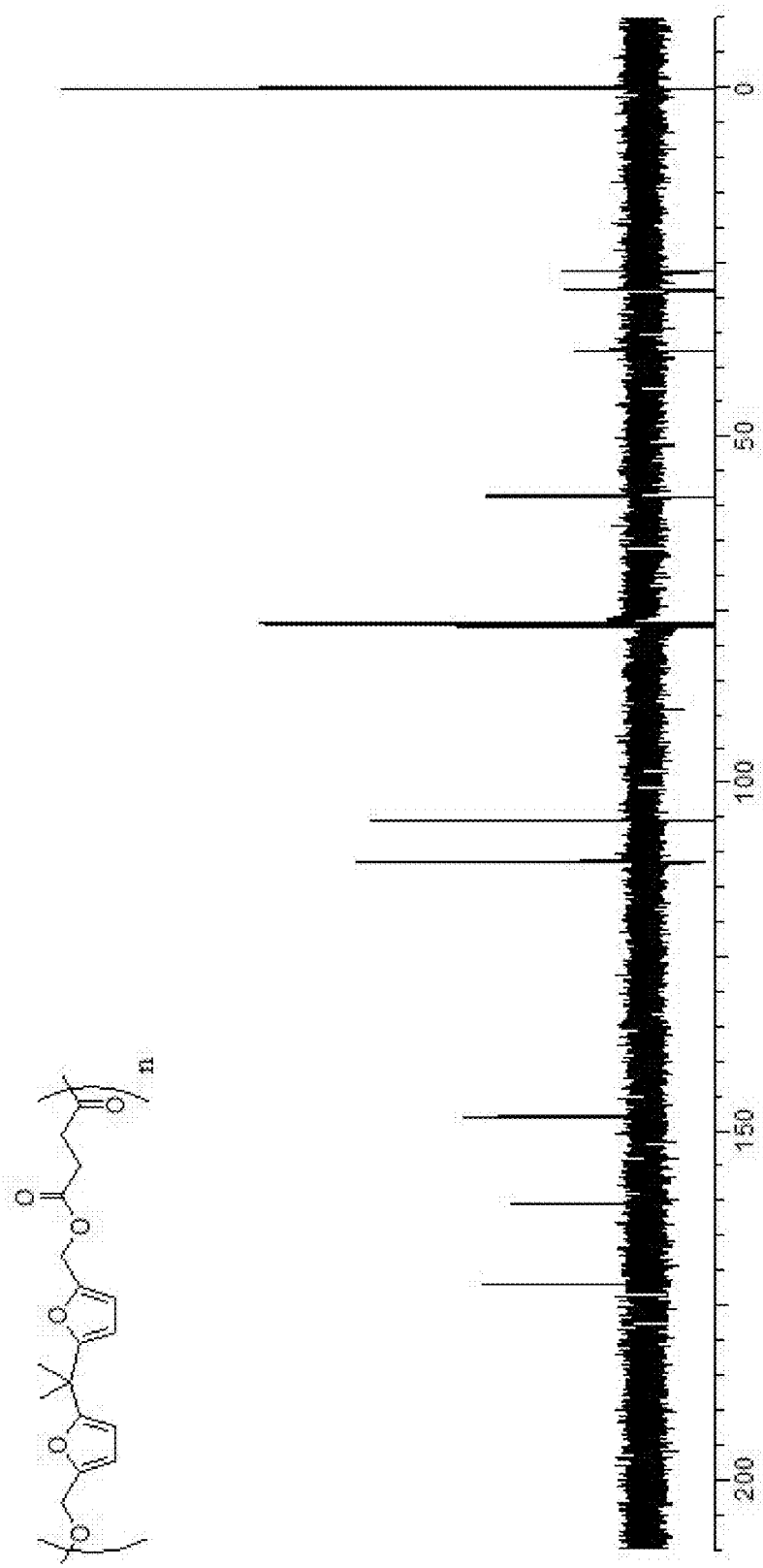
FIG. 27: $^{13}$C NMR spectrum of BFPE-1 (7).
Figure 28:
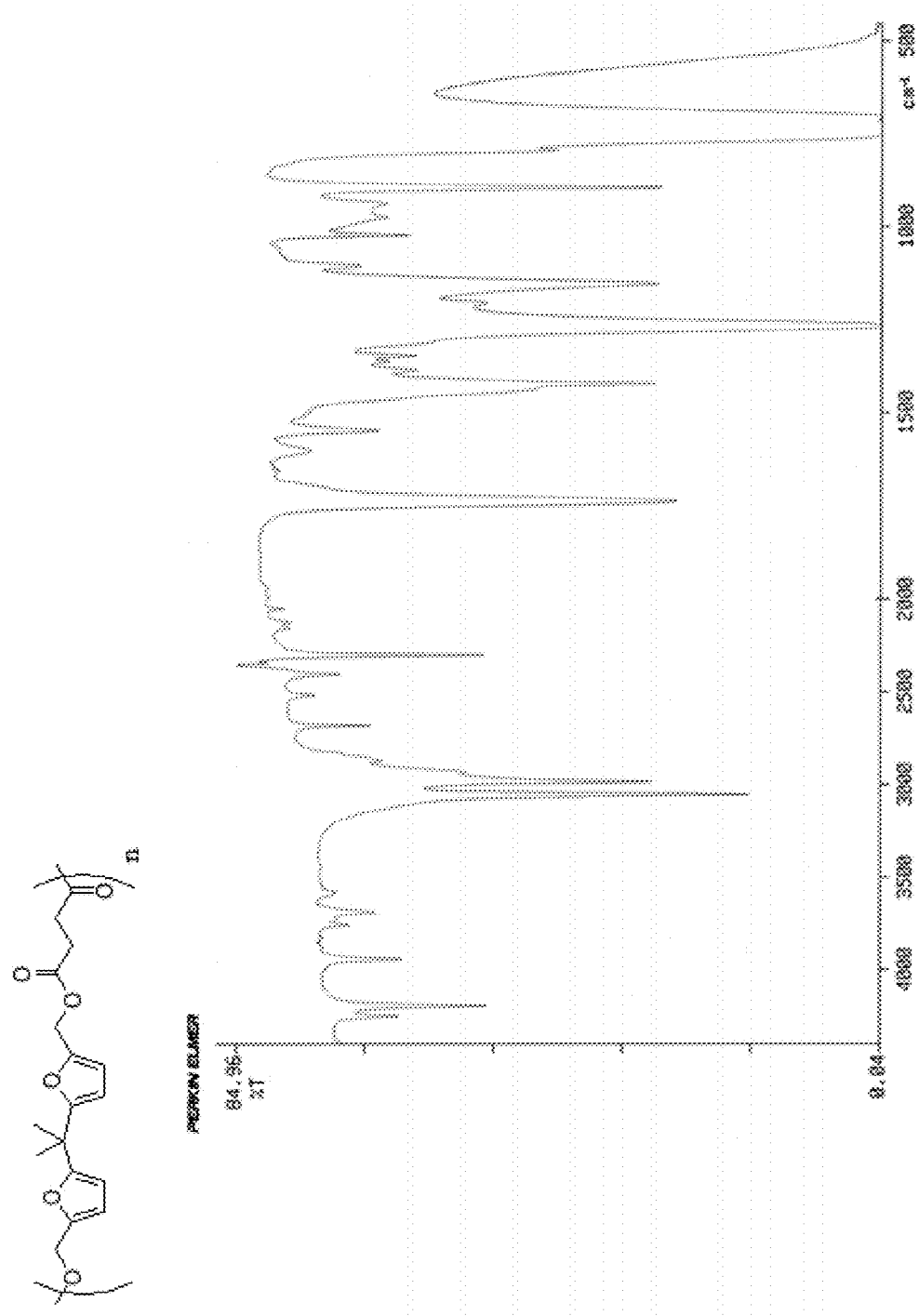
FIG. 28: IR spectrum of BFPE-1 (7).

BFPE-1, compound 7, was obtained via polycondensation of BFD compound 5 and succinic acid. BFD was subjected to esterification in 1,2-dichloroethane under nitrogen atmosphere with one equivalent succinic acid. N,N'-diisopropylcarbodiimide was used to activate the diacid, in the presence of a catalytic amount of N,N-dimethyl-4-aminopyridine. Briefly, BFD (0.52 mmol) was dissolved in 1,2-dichloroethane under $N_2$ atmosphere in a 50 ml round bottom flask. Succinic acid was added to the flask followed by N,N-dimethyl-4-aminopyridine and N,N'-diisopropylcarbodiimide. The reaction mixture was stirred at room temperature for a period of 15 hours. The reaction was intermittently checked for completion via precipitation from chloroform with methanol to monitor for precipitate. After completion, the bulk reaction mass was precipitated and washed three times with an excess of methanol. A cream colored sticky mass was obtained, which was further dried under high vacuum to obtain a cream colored solid (197 mg). $^1$H NMR (600 MHz, CDCl$_3$): δ 6.29 (d, 1H, J=3.0 Hz aromatic), 5.97 (d, 1H, J=3.6 Hz, aromatic), 5.01 (s, 2H, methylene-furan), 2.64 (s, 2H, methylene-succinate), 1.63 (s, 6H, methyl —CH$_3$). $^{13}$C NMR (150 MHz, CDCl$_3$): δ 172.12 (2C, carbonyl), 160.73 (2C, aromatic), 148.06 (2C, aromatic), 111.61 (2C, aromatic), 105.64 (2C, aromatic), 58.81 (2C, methylene), 37.78 (1C, furan bridge), 29.14 (4C, methylene-succinate), 26.39 (2C, methyl). FTIR (NaCl, cm$^{-1}$): 1750, C═O, strong. The $^1$H NMR and $^{13}$C NMR spectra of compound 7 are shown in FIG. 25 and FIG. 26, respectively, and the IR spectrum of compound 7 is shown in FIG. 27.

Figure 13A:
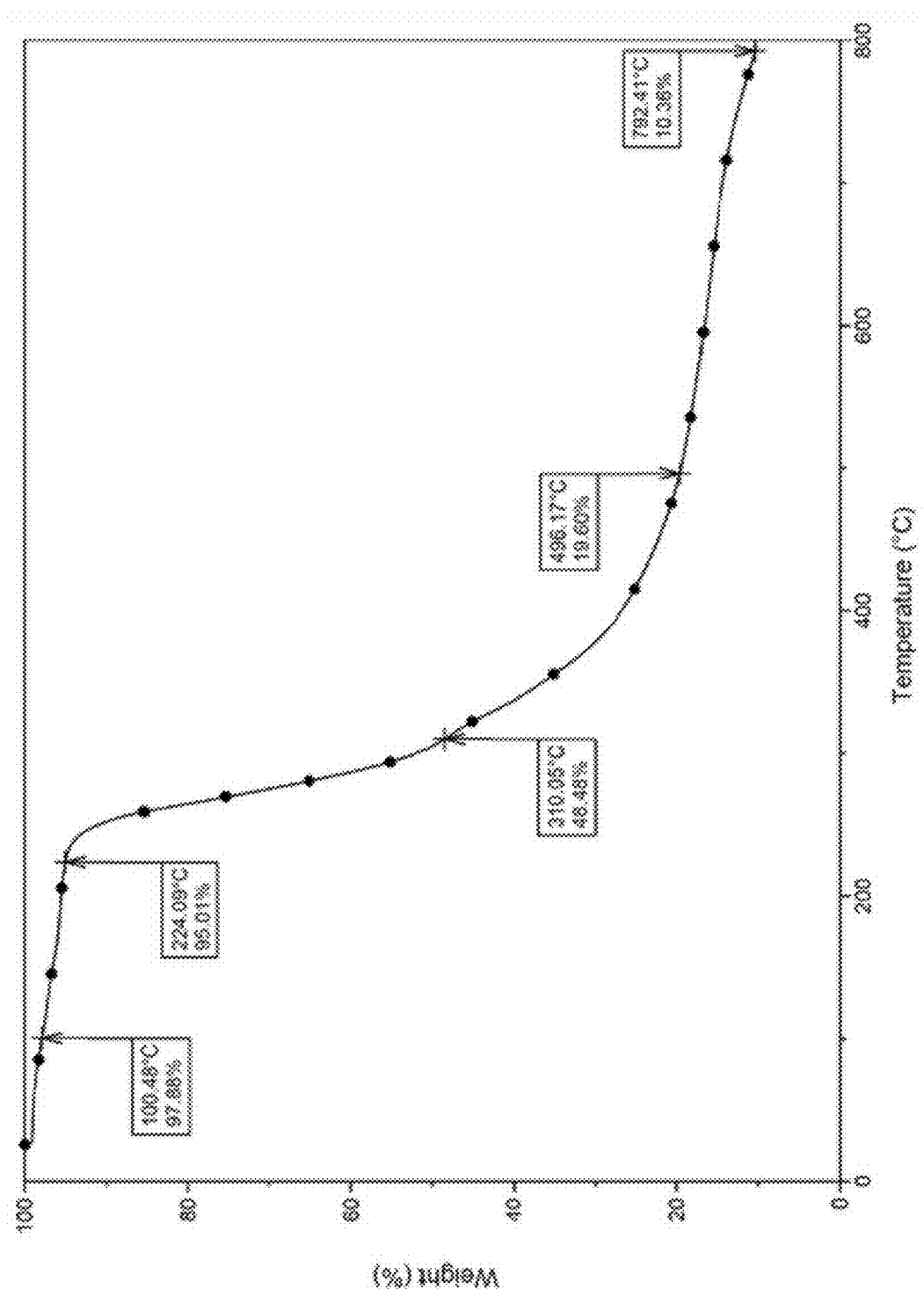
FIGS. 13A-13B: TGA thermograms of BFPE-1.
Figure 13B:
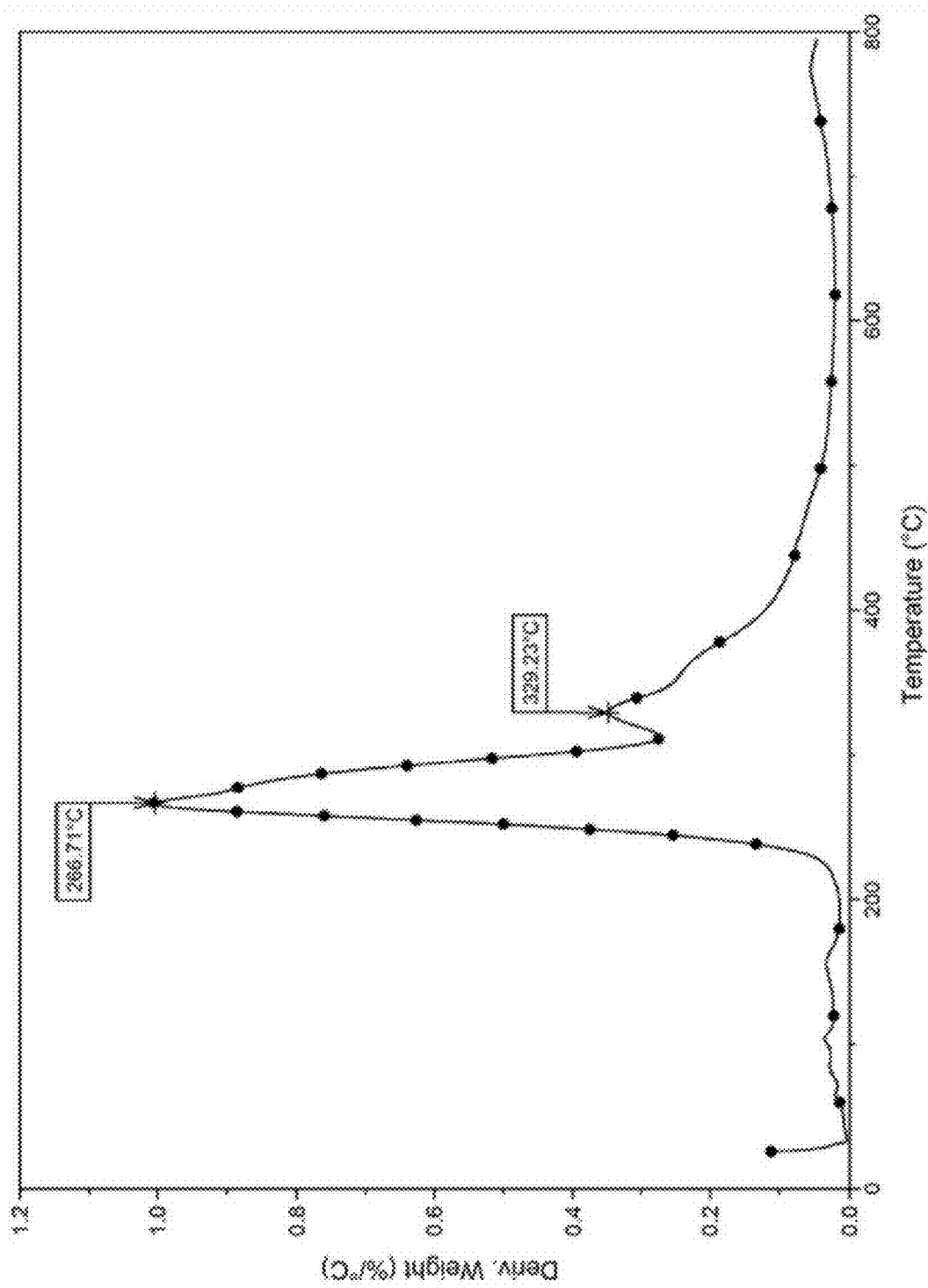

The thermal stability and weight loss due to decomposition of BFPE-1 was characterized using thermogravimetric analysis under flow of nitrogen 100 ml/min. As shown in FIG. 13A, at 100° C., the material showed a weight loss of ~2%, which may be from the evaporation of residual water. The start of thermal decomposition ($T_{start}$) was in the range of 100 to 225° C., which displays a weight loss of ~5% at around the latter temperature. A plot of derivative weight (%/° C.) versus temperature (° C.) reveals two-stage degradation of the material with two maximum ($T_{max}$), as seen in FIG. 13B. The $T_{max}$ for the first stage of degradation exhibited a value of 266° C., and 329° C. for the second stage. The corresponding weight loss at the end ($T_{end}$) of the two degradation stage temperature gave values of 48% and 20%, respectively.

Figure 14:
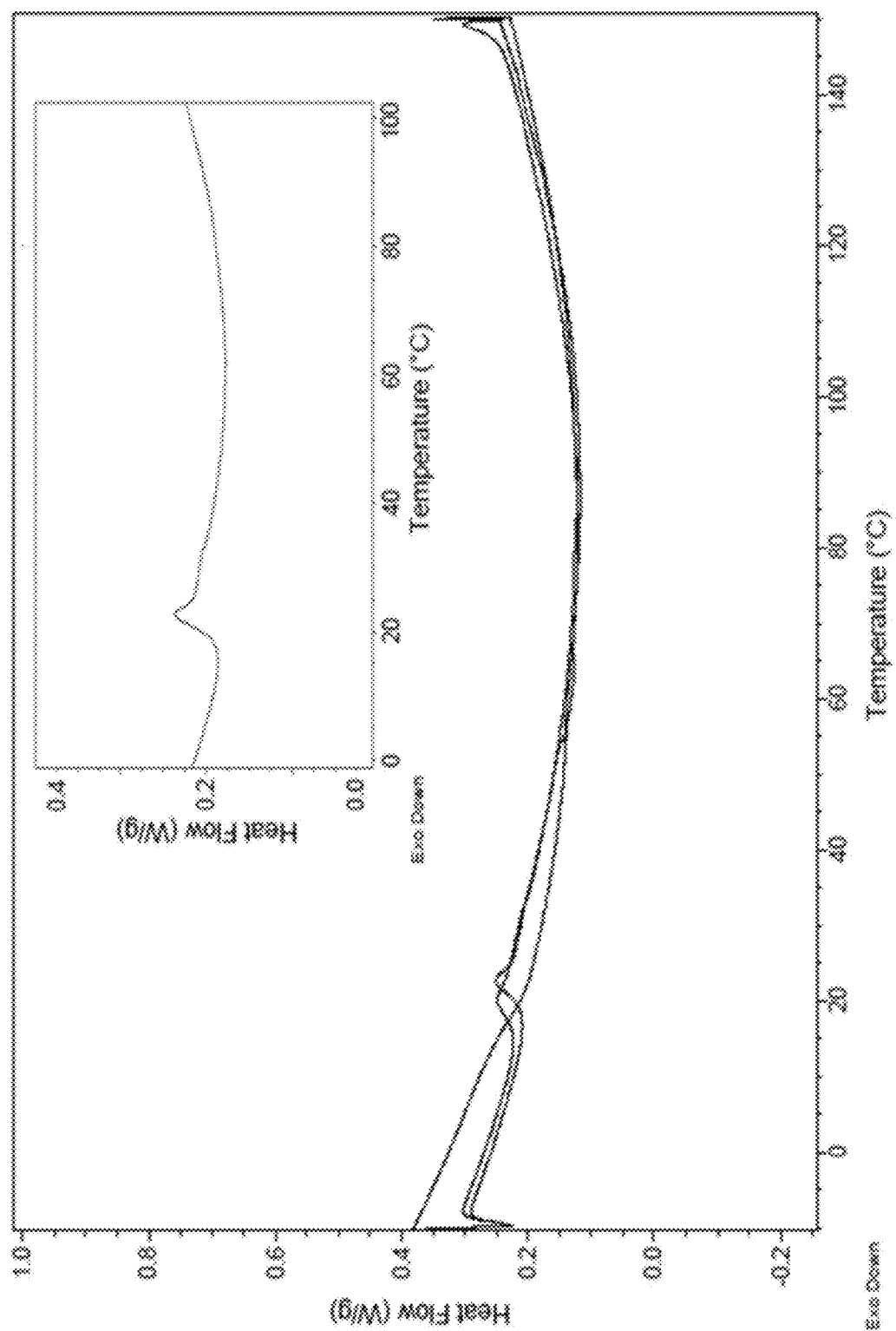
FIG. 14: DSC thermograms of BFPE-1 obtained during heat-cool-reheat cycle from −10° C. to 160° C. Inset shows glass transition (T) region from second heat (reheat) curve.

DSC measurements of BFPE-1 were carried out using a Perkin Elmer Pyris Diamond Differential Scanning Calorimeter with Intracooler, under nitrogen flow. The temperature and heat flow were calibrated using an indium standard. For initial analysis, a heat-cool-reheat cycle was performed from −40 to 300° C., by ramping 10° C./min, quenching at 300° C./min, and a reheat cycle to record glass transition ($T_g$) between 15-25° C., and degradation temperature ($T_d$) of 260° C. The absence of melt crystallization ($T_c$) and melting ($T_m$) indicates an amorphous nature of the synthesized polyester material. After preliminary scans, a heat-cool-reheat cycle was performed with the material from −10 to 160° C., by ramping 5° C./min, cooling at 5° C./min, and a reheat cycle to record $T_g$ of 20° C., and a $\Delta C_p$ of 0.676 J/g*° C. The DSC thermograms are shown in FIG. 14.

Figure 15A:
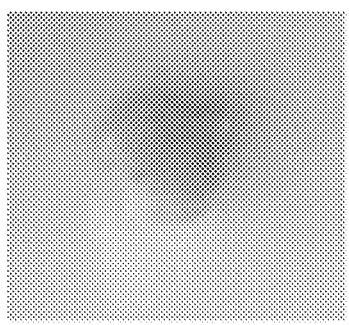
FIGS. 15A-15G: Images of BFPE-1 showing the external change of appearance with increasing temperature.
Figure 15B:
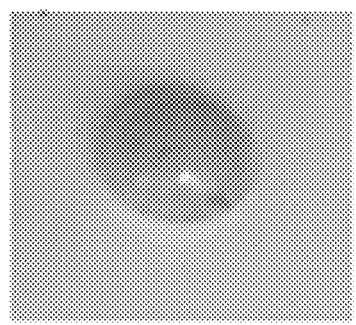
Figure 15C:
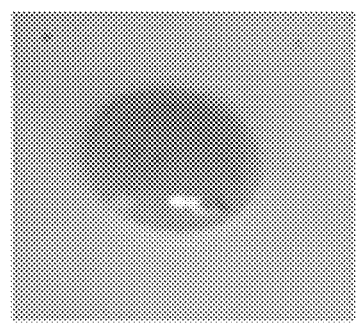
Figure 15D:
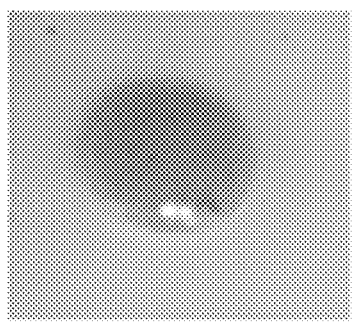
Figure 15E:
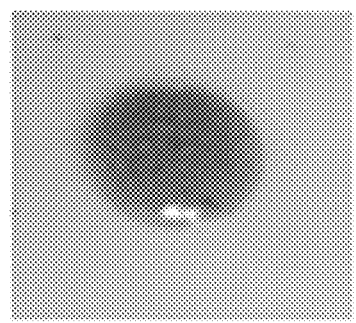
Figure 15F:
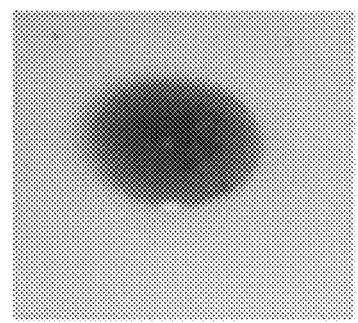
Figure 15G:
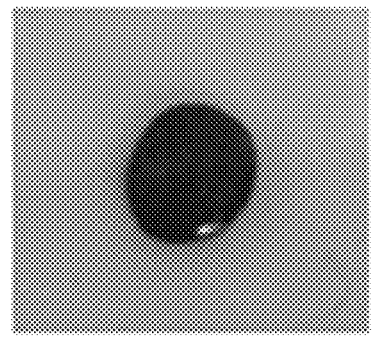

An open air melting point analysis was conducted to visualize the external changes by heating the BFPE-1 material from room temperature to 300° C. A change from solid to liquid between 70-100° C. was observed, as shown in FIGS. 15A, 15B. Increased liquefaction between 110-150° C., was observed, as shown FIGS. 15C, 15D. Further heating around 190° C. (FIG. 15E) resulted in a transparent material, and above 220° C. (FIG. 15F), the material began to char. This was followed by degradation around 270° C. (FIG. 15G).

Figure 16:
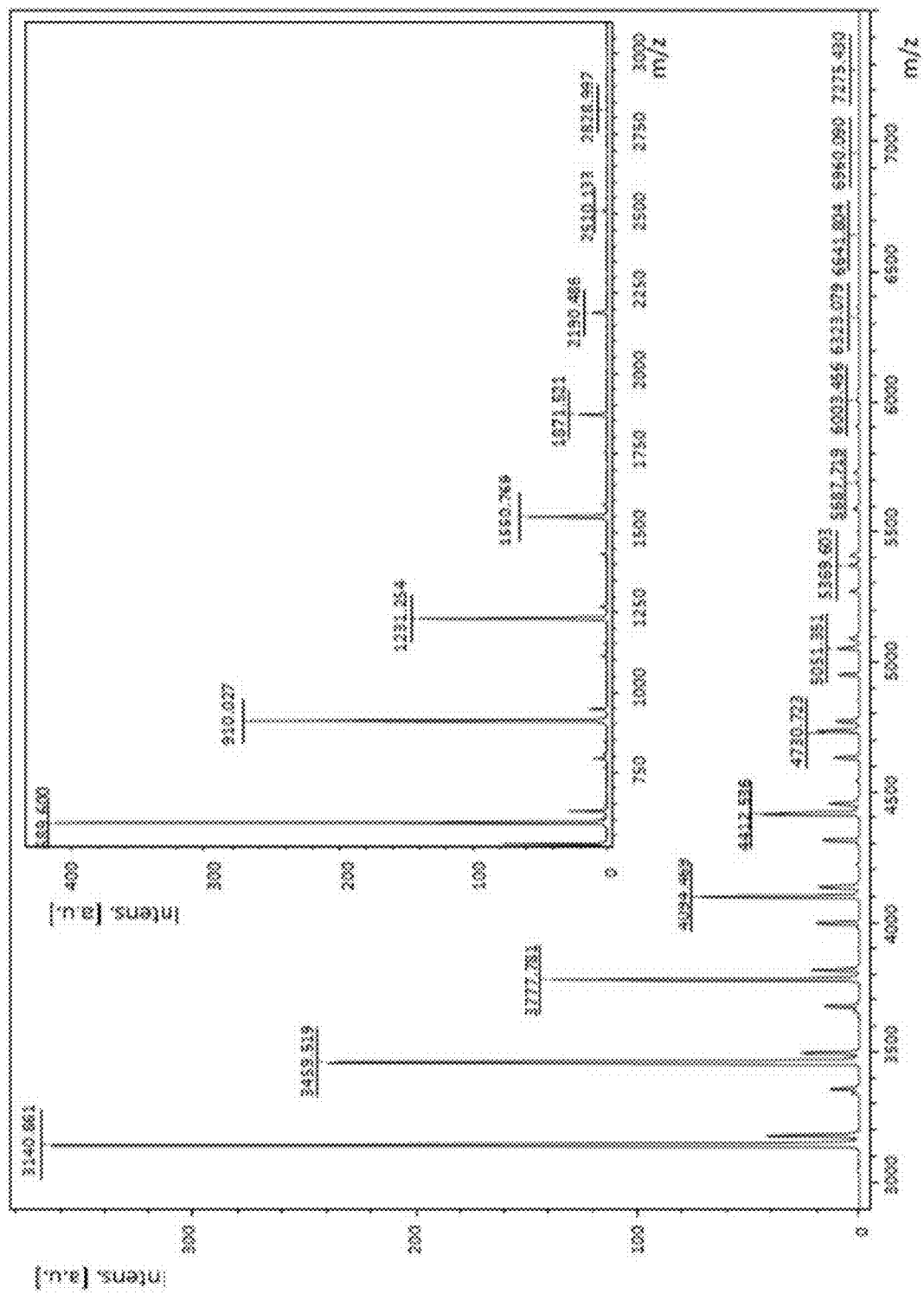
FIG. 16: MALDI-TOF/TOF mass spectrum of BFPE-1 with DHB matrix in range of 3 kDa to 7.5 kDa. The inset shows an expanded region between 0.5 kDa and 3 kDa.
Figures 17A, 17B:
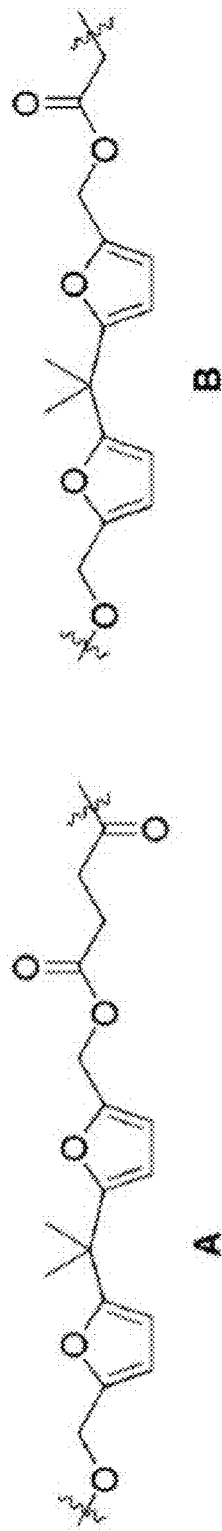
FIGS. 17A-17B: Structures of repeat 318 mass units (FIG. 17A) and fragmentation residue 276 mass units (FIG. 17B) of the BFPE from MALDI-TOF/TOF spectrum analysis.

A molecular weight determination of BFPE-1 was acquired using ultraflexXtreme MALDI-TOF/TOF mass spectrometer from Bruker Daltonics. MALDI matrices used for analysis of the BFPE-1 material were prepared using 2,5-dihydroxybenzoic acid (DHB) purchased from Sigma Aldrich Co. A mixture of 1:1 (v/v) of the polyester and DHB solution in acetone was mixed and deposited on the MALDI target plate, then dried under vacuum. The spectrum of BFPE-1, shown in FIG. 16, illustrates mass distribution in the range of 0.5-3.0 kDa (inset, FIG. 16) and 3-7.5 kDa (FIG. 16). A repeat of 318 mass units and a residue of 276 were identified from the MALDI spectrum. (FIGS. 17A-17B.)

Interpretation of number average molecular weight ($M_n$), weight average molecular weight ($M_w$), polydispersity index (PDI), degree of polymerization (DP), repeat units, and fragmentation residue were all carried out using PolyTools software from Bruker Daltonics. These values are shown in Table 3, below.

TABLE 3

MALDI-TOF/TOF Data Acquisition of BFPE-1 with PolyTools Software

| Range in kDa | Rep. Units | Residue | $M_n$ | $M_w$ | Pd | DP | % I |
|---|---|---|---|---|---|---|---|
| 3.0-7.5 | 318.177 | 276.278 | 5205.14 | 5219.87 | 1.00283 | 16.3592 | 12.1 |
| 0.5-3.0$^a$ | 318.597$^a$ | 269.751$^a$ | 1709.29$^a$ | 1869.79$^a$ | 1.04441$^a$ | 5.3651$^a$ | 3.2$^a$ |

$^a$Inset MALDI-TOF/TOF spectrum region between 0.5 and 3 kDa, FIG. 16.

Figure 18A:
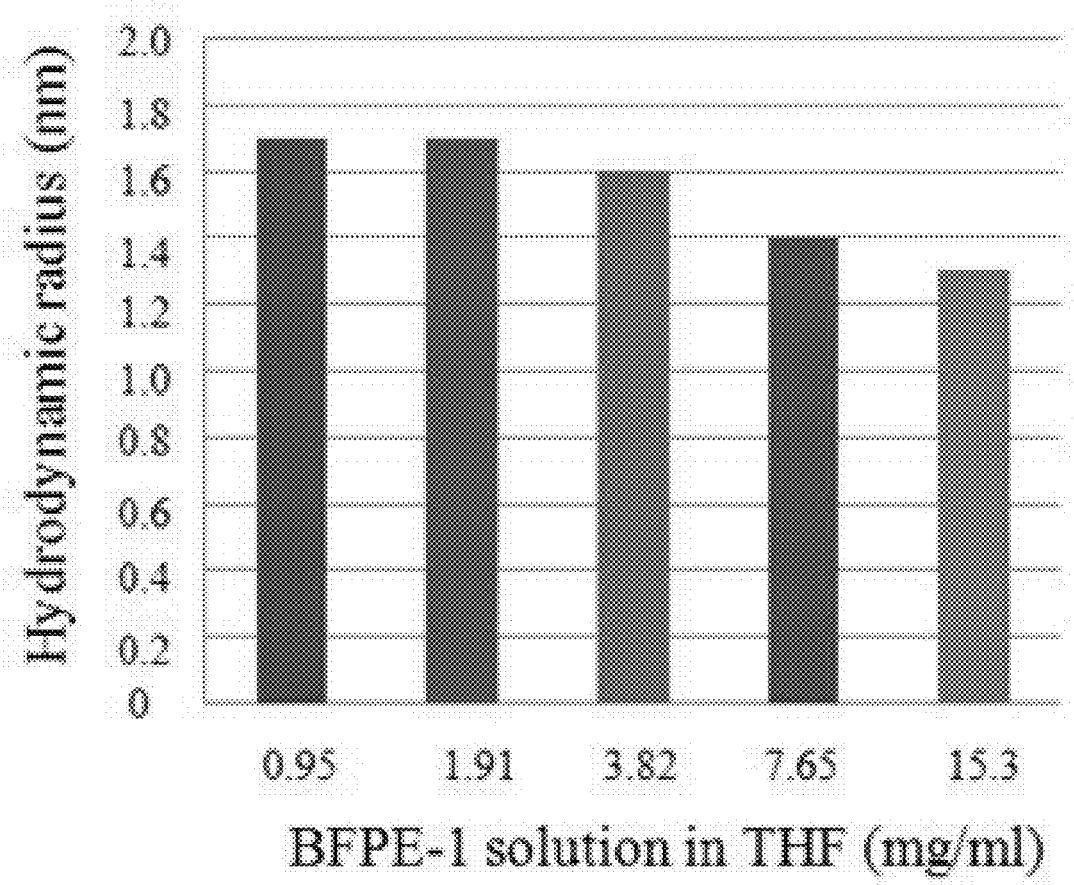
FIGS. 18A-18C: DLS plots of hydrodynamic radius (mm) versus BFPE-1 solution in THF (mg/ml) (FIG. 18A), % polydispersity versus BFPE-1 solution in THF (mg/ml) (FIG. 18B), and molecular weight (kDa) versus BFPE-1 solution in THF (mg/ml) (FIG. 18C).
Figure 18B:
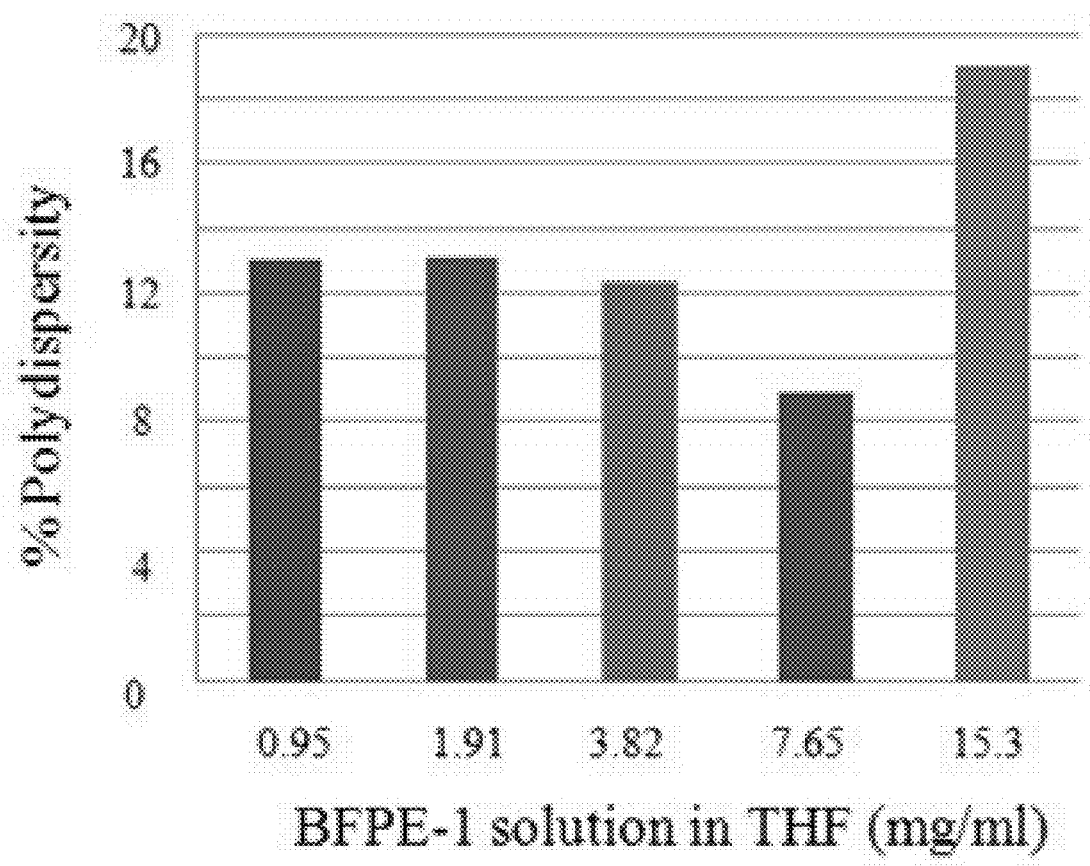
Figure 18C:
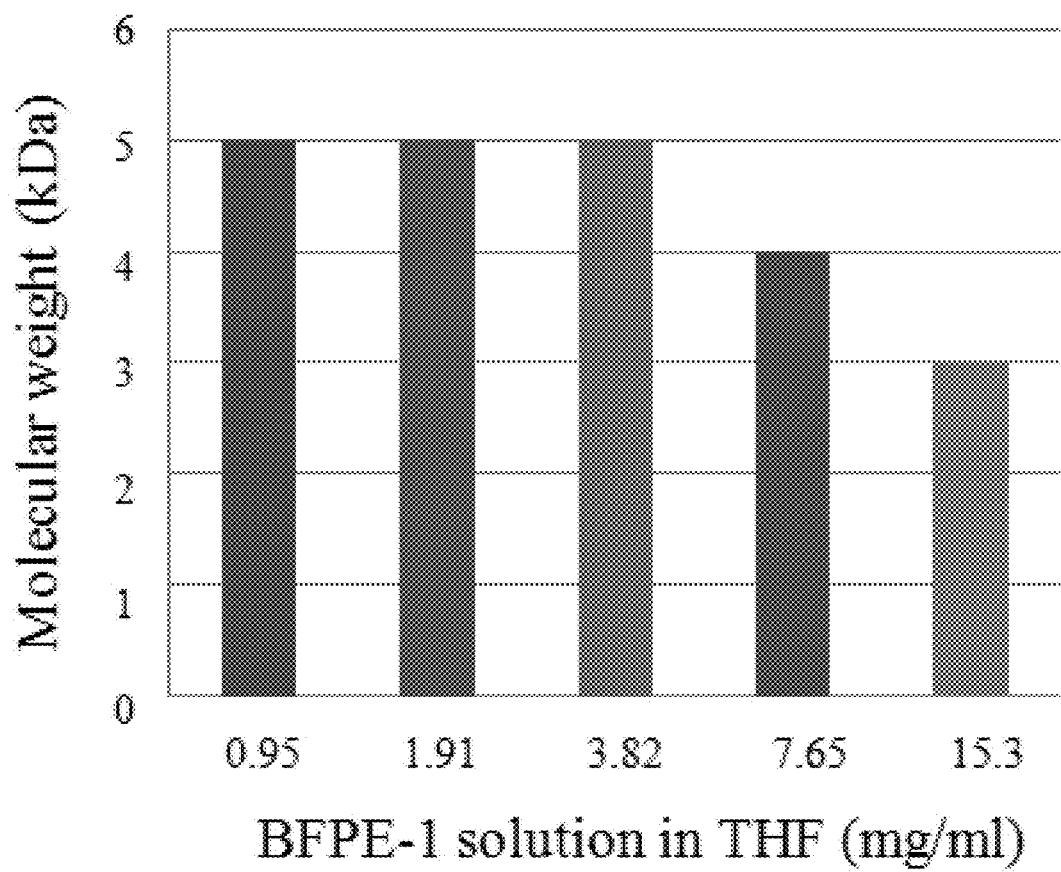

Investigation of the hydrodynamic radius ($R_H$), % polydispersity (% Pd), and molecular weight (kDa) of the synthesized BFPE-1 material was accomplished using dynamic light scattering (DLS) studies with varying concentration of PFSP at 25° C. Sample solutions were prepared in analytical grade tetrahydrofuran (THF) in 5 dilutions: 15.3 mg/ml, 7.65 mg/ml, 3.82 mg/ml, 1.91 mg/ml, and 0.95 mg/ml. Each dilution was subjected to five set repeats, with each set consisting of ten data points to ensure the acquisition of reproducible data. The DLS graphs, which are shown in FIGS. 18A-18C, were then plotted by averaging the accumulated data points for each concentration. The $R_H$ of the BFPE-1 was found to be within a range of 1.3-1.7 nm (FIG. 18A). Slight swelling of the material is illustrated from this plot with increasing dilution. The % Pd was in a range of 13-19%, representing a highly monodisperse solution (FIG. 18B). The average molecular weight of the synthesized polyester was found to be in a limit of 3 to 5 kDa (FIG. 18C). This result is in agreement with the MALDI-TOF/TOF data, which represents an average molecular weight of 5 kDa.

The above examples show the conversion of furfural to BFD via a short synthetic route, and the use of BFD as a feedstock for producing BFPE-1. The BFD can also be employed in generating other BF-based polymers, such as, but not limited to: polyesters, polyamides, polether, polycarbonates, and polyurethanes. X-ray crystallography provided insight into the atomic and molecular structure of BFD, which is important for polymerization applications. The above-described characterization of the synthesized polyester BFPE-1 shows that BFD can be used as a monomeric unit in polymer development.

Certain embodiments of the methods disclosed herein are defined in the above examples. It should be understood that these examples, while indicating particular embodiments of the invention, are given by way of illustration only. From the above discussion and these examples one skilled in the art can ascertain the essential characteristics of this disclosure, and without departing from the spirit and scope thereof, can make various changes and modifications to adapt the compositions and methods described herein to various usages and conditions. Various changes may be made and equivalents may be substituted for elements thereof without departing from the essential scope of the disclosure. In addition, many modifications may be made to adapt a particular situation or material to the teachings of the disclosure without departing from the essential scope thereof.

What is claimed is:

1. A composition comprising Formula I:

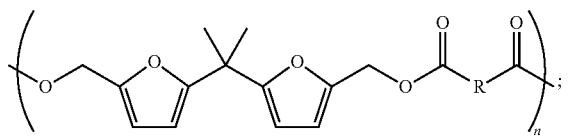

Formula I wherein:
R is $C_6H_4$ or $(CH_2)_x$, wherein x is from 1 to 10; and
n is from 10 to 10,000;
and salts, stereoisomers, polymorphs, racemates, solvates, and hydrates thereof.

2. The composition of claim 1, wherein the composition comprises monomeric units having a structural formula of Formula II:

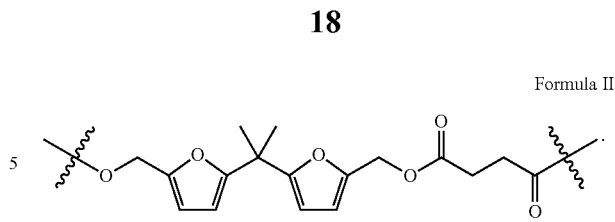

Formula II

3. The composition of claim 1, wherein the composition comprises Formula III:

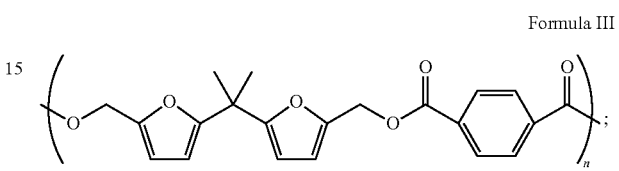

Formula III wherein n is from 10 to 10,000.

4. The composition of claim 1, wherein the composition comprises Formula IV:

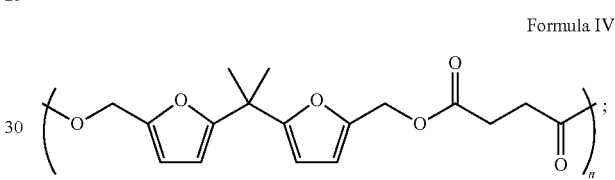

Formula IV wherein n is from 10 to 10,000.

5. A composition comprising Formula VI:

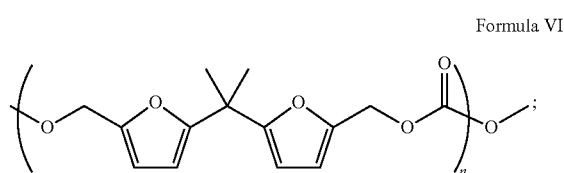

Formula VI wherein n is from 10 to 10,000;
and salts, stereoisomers, polymorphs, racemates, solvates, and hydrates thereof.

* * * * *